(12) United States Patent
Su et al.

(10) Patent No.: US 7,105,301 B2
(45) Date of Patent: Sep. 12, 2006

(54) DETECTING MOLECULAR BINDING BY MONITORING FEEDBACK CONTROLLED CANTILEVER DEFLECTIONS

(75) Inventors: Xing Su, Cupertino, CA (US); Selena Chan, San Jose, CA (US); Tae-Woong Koo, South San Francisco, CA (US); Mineo Yamakawa, Campbell, CA (US); Andrew A. Berlin, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 199 days.

(21) Appl. No.: 10/667,776

(22) Filed: Sep. 22, 2003

(65) Prior Publication Data

US 2004/0115711 A1 Jun. 17, 2004

Related U.S. Application Data

(63) Continuation-in-part of application No. 10/254,201, filed on Sep. 24, 2002.

(51) Int. Cl.
*C12Q 1/68* (2006.01)
*C12Q 1/70* (2006.01)
*G01N 33/566* (2006.01)
*G01N 33/563* (2006.01)

(52) U.S. Cl. .............. 435/6; 435/5; 436/501; 436/512

(58) Field of Classification Search .......... 422/80, 422/82.01, 82.02, 82.05; 435/6
See application file for complete search history.

(56) References Cited

U.S. PATENT DOCUMENTS

| | | | |
|---|---|---|---|
| 5,106,729 A | 4/1992 | Lindsay et al. | |
| 5,607,568 A | 3/1997 | Zenharusern et al. | |
| 5,739,425 A | 4/1998 | Binning et al. | |
| 5,866,328 A | 2/1999 | Bensimon et al. | |
| 6,016,686 A * | 1/2000 | Thundat | 73/23.2 |
| 6,033,852 A | 3/2000 | Andle et al. | |
| 6,073,484 A | 6/2000 | Miller et al. | |
| 6,079,255 A | 6/2000 | Binnig et al. | |
| 6,092,422 A | 7/2000 | Binnig et al. | |
| 6,123,819 A | 9/2000 | Peeters | |
| 6,194,148 B1 | 2/2001 | Hori et al. | |
| 6,280,939 B1 | 8/2001 | Allen | |
| 6,310,189 B1 | 10/2001 | Fodor et al. | |
| 6,325,904 B1 | 12/2001 | Peeters | |
| 6,379,895 B1 | 4/2002 | Fodor et al. | |
| 6,436,647 B1 | 8/2002 | Quate et al. | |
| 2002/0102743 A1 | 8/2002 | Majumdar et al. | |

FOREIGN PATENT DOCUMENTS

| | | |
|---|---|---|
| WO | WO 97/09584 | 3/1997 |
| WO | WO 00/14539 | 3/2000 |
| WO | WO 00/58729 | 10/2000 |
| WO | WO 01/33226 A1 | 5/2001 |

OTHER PUBLICATIONS

Abadal, et al., "Non-Linear Static and Dynamic Behaviour of an Electrostatically Excited Nanocantilever: Electrical Modelization and AFM Characterization, " 9th MEL-ARI/NID Workshop: Feb. 6-8, 2002, Catania, Italy, 2 pages.

Abadel, et al., "Fabrication and Modelling of a Nano-Cantilever for the Development of Sub-Picogram Sensitivity Mass Sensor," TNT2000, 16th-20th Oct. 2000, Toledo, Spain, 1 page.

Augustin, et al., "Progress Towards Single-Molecule Sequencing: Enzymatic Synthesis of Nucleotide-Specifically Labeled DNA," Journal of Biotechnology 86 (2001) 289-301.

Ballato, "Modeling Piezoelectric and Piezomagnetic Devices and Structures via Equivalent Networks," *IEEE Transactions on Ultrasonics, Ferroelectrics, and Frequency Control*, vol. 48, No. 5, Sep. 2001 1189-1240.

Baller, et al., "A Cantilever Array-Based Artificial Nose," Ultramicroscopy 82 (2000) 1-9.

Bardea, et al, "Amplified Microgravimetic Quartz-Crystal-Microbalance Analyses of Olignucleotide Complexes: A Route to a Tay-Sachs Biosensor Device," *Chem., Commun.*, 1998 839-840.

Bennink, et al., "Single-Molecule Manipulation of Double-Stranded DNA Using Optical Tweezers: Interaction Studies of DNA with RecA and YOYO-1," *Cytometry*, 36: 200-208, 1999.

(Continued)

*Primary Examiner*—Young J. Kim
(74) *Attorney, Agent, or Firm*—DLA Piper Rudnick Gray Cary US LLP

(57) ABSTRACT

The present methods and apparatus concern the detection and/or identification of target analytes using probe molecules. In various embodiments of the invention, the probes or analytes are attached to one or more cantilevers. Binding of a probe to an analyte results in deflection of the cantilever, detected by a detection unit. A counterbalancing force may be applied to restore the cantilever to its original position. The counterbalancing force may be magnetic, electrical or radiative. The detection unit and the mechanism generating the counterbalancing force may be operably coupled to an information processing and control unit, such as a computer. The computer may regulate a feedback loop that maintains the cantilever in a fixed position by balancing the deflecting force and the counterbalancing force. The concentration of analytes in a sample may be determined from the magnitude of the counterbalancing force required to maintain the cantilever in a fixed position.

13 Claims, 6 Drawing Sheets

OTHER PUBLICATIONS

Bhansali, "Research: Nanoporous Silica/Piezoelectric Cantilevers for Biosensing Applications," Retrieved from the Internet Mar. 1, 2002, http://www.princeton.edu/~cml/html/_ research/biosensor.html, 3 pages.

Cullum, et al., "The Development of Optical Nanosensors for Biological Measurements," *Trends in Biotech*, Sep. 2000, vol. 18, 388-393.

Davis, et al., "Nano-Resonators for High Spatial Resolution Mass Detection," Retrieved from the Internet Dec. 13, 2002, http://www.nbi.dk/dfs/abs2000.ff16.html, 1 page.

Fabian, et al., "Fabrication of Micromechanical Cantilever Sensors for Nanoscale Thermal Detection," PSI Annual Report 1999, 1 page.

Fritz, et al., "Translating Biomolecular Recognition into Nanomechanics," *Science*, vol. 288, Apr. 2000, 2 pages.

George, "Microcantilever Sensor Research," Retrieved from the Internet Jan. 21, 2002, http://www.chemistry.uah.edu/faculty/george/cantilever.html, 2 pages.

Hansen, et al., "Cantilever-Based Optical Deflection Assay for Discrimination of DNA Single-Nucleotide Mismatches," *Anal. Chem.*, 2001, 73, 1567-1571.

Harley, "Advances in Piezoresistive Probes for Atomic Force Microscopy," A dissertation submitted to the Department of Mechanical Engineering and the Committee on Graduate Studies of Stanford University in partial fulfillment of the requirements for the Degree of Doctor of Philosophy, Mar. 2000, 140 pages.

Ilic, et al., "Mechanical Resonant Immunospecific Biological Detector," *Applied Physics Letters*, vol. 77, No. 3, Jul. 2000, 450-452.

Jensenius, et al., "Micromechanical Bioprobes," Retrieved from the Internet Jan. 21, 2002, http://www.nbi.dk/~biophys—meeting 99/abs44.html, 1 page.

Koll, et al., "CMOS-Based Chemical Microsensors and Microsystems," Retrieved from the Internet Mar. 1, 2002, http://www.iqe.ethz.ch/pel/annrep/annrep99/JB99_PEL_08.html, 5 pages.

Lang, et al., "An Electronic Nose Based in a Micromechanical Cantilever Array" Retrieved from the Internet, www.chem.ucla.edu/dept/Faculty/gimzewski/pub/UTAS.pdf, 4 pages.

Lang, et al., "Sequential Position Readout from Arrays of Microchemical Cantilever Sensors," *Appl. Phys. Lett.*, 72(3), Jan 1998, 383-385.

Lang, et al., "An Artifical Nose Based on a Micromechanical Cantilever Array," *Analytica Chimica Acta*, 393 (1999) 59-65.

Mehta, et al., "Single-Molecule Biomechanics with Optical Methods," *Science*, vol. 283, Mar. 1999, 7 pages.

Müller, et al., "Electrostatically Balanced Subnanometer Imaging of Biological Specimans by Atomic Force Microscope," *Biophysical Journal*, vol. 76, Feb. 1999, 1101-1111.

Smith, et al., "Inexpensive Optical Tweezers for Undergraduate Laboratories," *Am. J. Phys.*, 67 (1), Jan 1999, pp. 26-35.

Tamayo, et al., "High-Q Dynamic Force Microscopy in Liquid and Its Application to Living Cells," *Biophysical Journal*, vol. 81, Jul. 2001, 526-537.

Voldman, et al, "Microfabrication in Biology and Medicine," *Annu. Rev. Biomed. Eng.*, 1999, 401-425.

Walker, et al., "Mechanical Manipulation of Bone and Cartilage Cells with 'Optical Tweezers'," *FEBS Letters*, 459 (1999) pp. 39-42.

Wilson, "A Practical Approach to Vibration Detection and Measurement," Retrieved from the Internet Feb. 4, 2002, http://www.sensormag.com/articles/0299/prac0299/mail.shtml, 19 pages.

Wu, et al., "Origin of Nanomechanical Cantilever Motion Generated from Biomolecular Interaction," *PNAS*, vol. 98, No. 4, Feb. 2001, 1560-1564.

Yamaguchi, et al., "Adsorption, Immobilization, and Hybridization of DNA Studied by the Use of Quartz Crystal Oscillators," *Anal. Chem.* 1993, 65, 1925-1927.

Zhou, et al., "Microgravimetric DNA Sensor Based on Quartz Crystal Microbalance: Comparison of Oligonucleotide Immobilization Methods and the Application in Genetic Diagnosis," *Biosensors and Bioelectronics*, 16 (2001) 85-95.

"Single Cell Detection Using Micromechanical Oscillators," Biology and Chemistry, Project # 762-99, Retrieved from the Internet on Jan. 7, 2003, URL:///<www.nnf.cornell.edu/2001cnfra/200138.pdf> 2 pages.

"Nanomechanical Cantilever Array Sensors," Retrieved from the Internet on Jan. 7, 2003, URL:///<http://monet.physik.unibas.ch/nose/inficon> 5 pages.

"Cantilever Arrays; Biochemical Sensor; DNA Sensor; Mass Sensor; and Measurement Setup," Retrieved from the Internet on Jan. 21, 2002, URL:///<http://www.zurich.ibm.com/st/nanoscience/arrays.html> 8 pages.

"Thermogravimetry," Retrieved from the Internet on Mar. 8, 2002, URL:///<http://www.zurich.ibm.com/st/nanoscience/thermogravimetry.html> 2 pages.

"Electrostatic Force-Feedback Force Sensor," Retrieved from the Internet on Mar. 29, 2002, URL:///<http://www.ifm.liu.se/Applyphys/spm/instruments/forcefeedback.html> 2 pages.

Baselt, David R. et al., "Biosensor based on force microscope technology", *J. Vac. Sci. Technol. B.*, vol. 14, No. 2, pp. 789-793, 1996.

Bloch, Immanuel et al., "Optics with an Atom Laser Beam", *The American Physical Society.*, vol. 87, No. 3, pp. 030401-1-030401-4, 2001.

Dutta, P. et al., "Enantioselective Sensors Based on Antibody-Mediated Nanomechanics", *Analytical Chemistry*, vol. 75, No. 10, pp. 2342-2348, 2003.

Fritz, J. et al., "Translating Biomolecular Recognition into Nanomechanics", *Science*, vol. 288, pp. 316-318, 2000.

Han, J. and Craighead, H.G., "Separation of Long DNA Molecules in a Microfabricated Entropic Trap Array", *Science*, vol. 288, pp. 1026-1029, 2000.

Guanghua, Wu et al, "Bioassay of prostate-specific antigen (PSA) using microcantilevers", *Nature Biotechnology*, vol. 19, pp. 856-860, 2001.

* cited by examiner

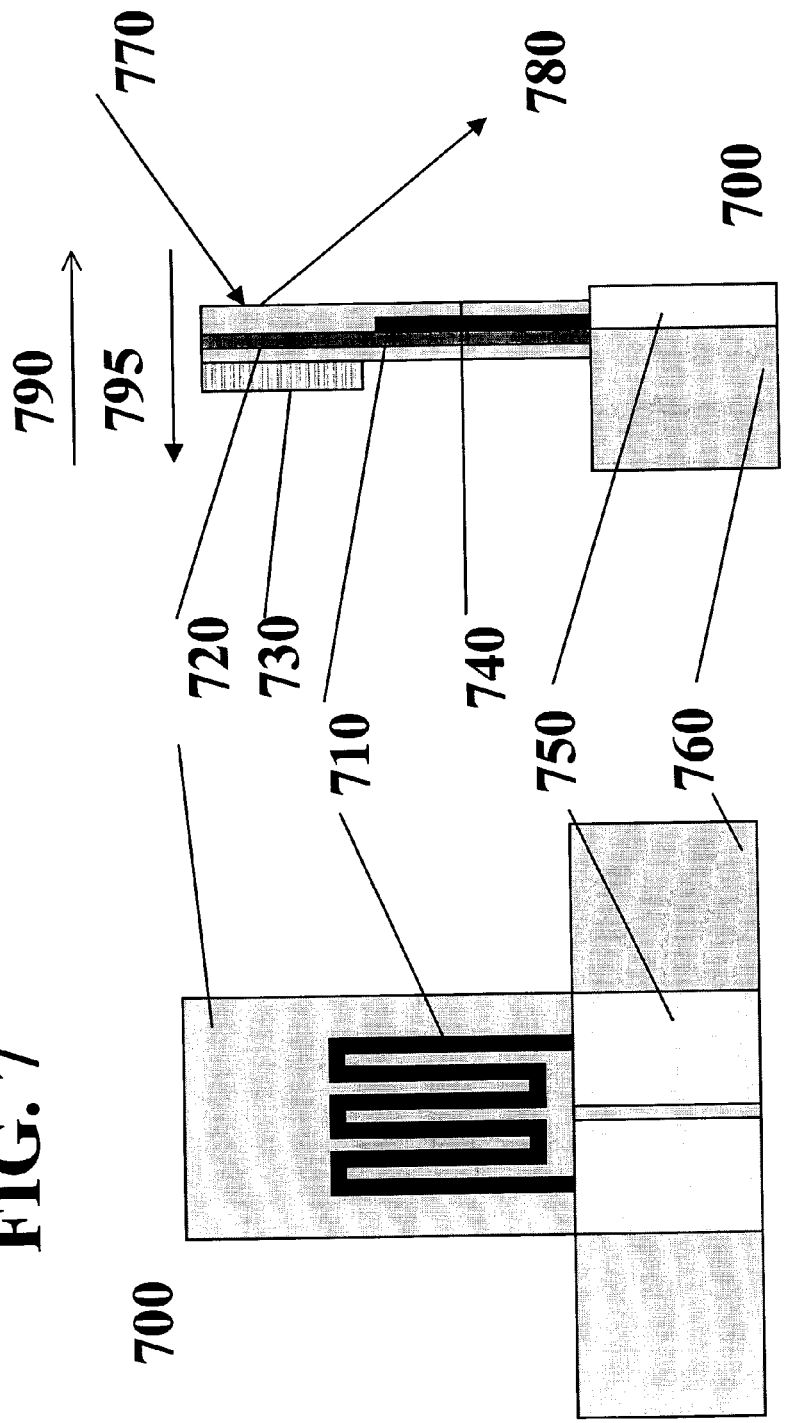

DETECTING MOLECULAR BINDING BY MONITORING FEEDBACK CONTROLLED CANTILEVER DEFLECTIONS

This application is a Continuation-In-Part of Ser. No. 10/254,201, filed on Sep. 24, 2002, entitled "Detecting Molecular Binding by Monitoring Feedback Controlled Cantilever Deflections," currently pending and claims priority thereof.

BACKGROUND OF THE INVENTION

1. Field of the Invention

The methods and apparatus 100, 200, 300 described herein relate to the field of analyte detection and/or identification. In particular, the disclosed methods and apparatus 100, 200, 300 relate to the use of feedback-controlled cantilever 110, 210, 310, 400, 510 deflection for analyte detection and/or identification.

2. Related Art

Various methods have been used for detection and/or identification of biomolecule analytes, such as proteins, peptides, receptors, nucleic acids, hormones, metabolites, etc. Antibody based assays have been used to detect and/or identify a large number of analytes. Any compound, composition, molecule or aggregate for which a specific binding antibody can be made may be detected by a variety of immunoassay techniques, such as ELISA, Western blotting, etc. In general, either the analyte (antigen) of interest, or an antibody against the analyte of interest, is attached to a solid support. If the analyte is bound to the support, an antibody that binds to the analyte may be labeled with a fluorescent, enzymatic or other label and attachment of the antibody to the bound analyte may be detected. If a first antibody is bound to the support, binding of analyte to the first antibody may be detected by binding of a second, labeled antibody to the analyte (sandwich assay). Antibody based assays may occasionally show unacceptably high levels of false positive or false negative results, due to cross-reactivity of the antibody with different antigens, low antigenicity of the target analyte (leading to low sensitivity of the assay), non-specific binding of antibody to various surfaces, etc.

Oligonucleotide hybridization based assays are in wide use for detection of target oligonucleotides, messenger ribonucleic acids (mRNAs), genomic deoxyribonucleic acid (DNA), etc. In such assays, a probe oligonucleotide that is complementary in sequence to a nucleic acid target analyte is labeled and allowed to hybridize to a sample suspected of containing the target nucleic acid. Many variations on this technique are known, such as Southern blotting, dot-blotting or slot-blotting. More recently, DNA chips have been designed that can contain hundreds or even thousands of individual oligonucleotide probes. Hybridization of a target nucleic acid to a probe oligonucleotide may be detected using fluorescent labels, radioactivity, etc. Problems with sensitivity and/or specificity of such assays may arise. Nucleic acid hybridization may occur between sequences that are not precisely complementary through mismatch hybridization, leading to false positive results.

Other types of analyte detection assays are known, such as enzyme activity assays, receptor-ligand binding assays, etc. As with the techniques discussed above, selectivity and/or sensitivity problems may arise with any standard detection technique. A need exists in the field for selective, highly sensitive methods of detecting and/or identifying various analytes.

BRIEF DESCRIPTION OF THE DRAWINGS

The following drawings form part of the specification and are included to further demonstrate certain embodiments of the invention. The embodiments may be better understood by reference to one or more of these drawings in combination with the detailed description presented herein.

FIG. 7 illustrates an exemplary cantilever 700 including a horizontally symmetric heater (710) (not to scale).

DETAILED DESCRIPTION OF ILLUSTRATIVE EMBODIMENTS

Definitions

Figure 1:
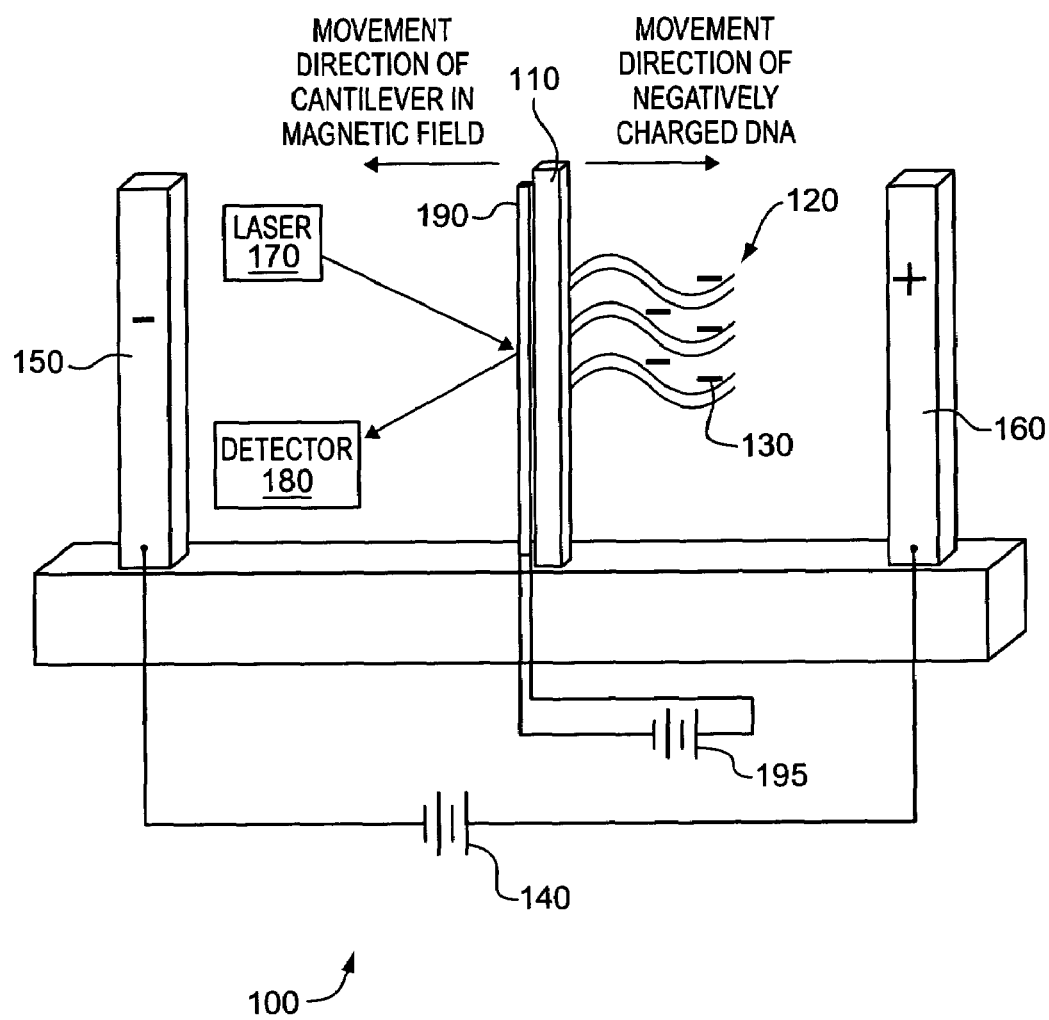
FIG. 1 illustrates an exemplary apparatus 100 (not to scale) and method for analyte 130 detection using a charge-magnet-balanced cantilever 110 system.

As used herein, "a" and "an" may mean one or more than one of an item.

As used herein, "about" means within plus or minus five percent of a number. For example, "about 100" means any number between 95 and 105.

As used herein, "operably coupled" means that there is a functional interaction between two or more units. For example, a detection unit may be "operably coupled" to a surface if the detection unit is arranged so that it may detect changes in the properties of the surface, such as the position or curvature of the surface.

"Analyte" 130, 230, 330 and "target" 130, 230, 330 mean any molecule, compound, composition or aggregate of interest for detection and/or identification. Non-limiting examples of analytes 130, 230, 330 include an amino acid, peptide, polypeptide, protein, glycoprotein, lipoprotein, antibody, nucleoside, nucleotide, oligonucleotide, nucleic acid, sugar, carbohydrate, oligosaccharide, polysaccharide, fatty acid, lipid, hormone, metabolite, growth factor, cytokine, chemokine, receptor, neurotransmitter, antigen, allergen, antibody, substrate, metabolite, cofactor, inhibitor, drug, pharmaceutical, nutrient, prion, biohazardous agent, infectious agent, prion, vitamin, heterocyclic aromatic compound, carcinogen, mutagen and/or waste product. "Analytes" 130, 230, 330 are not limited to single molecules or atoms, but may also comprise complex aggregates, such as a virus, bacterium, *Salmonella, Streptococcus, Legionella, E. coli, Giardia, Cryptosporidium, Rickettsia*, spore, mold, yeast, algae, *amoebae*, dinoflagellate, unicellular organism, pathogen or cell. In certain embodiments, cells exhibiting a particular characteristic or disease state, such as a cancer cell, may be target analytes 130, 230, 330. Virtually any chemical or biological compound, molecule or aggregate could be a target analyte 130, 230, 330.

"Probe" 120, 220, 320, 520 refers to any molecule that can bind selectively and/or specifically to an analyte 130, 230, 330 of interest. Probes 120, 220, 320, 520 include but are not limited to antibodies, antibody fragments, single-chain antibodies, genetically engineered antibodies, oligonucleotides, polynucleotides, nucleic acids, nucleic acid analogues, proteins, peptides, binding proteins, receptor proteins, transport proteins, lectins, substrates, inhibitors, activators, ligands, hormones, cytokines, etc.

The methods and apparatus 100, 200, 300 disclosed herein are of use for the rapid, sensitive detection and/or identification of analytes 130, 230, 330. In certain embodiments of the invention, analytes 130, 230, 330 may be detected and/or identified with sensitivity as low as a single analyte 130, 230, 330 molecule. In some embodiments of the invention, the ability to detect and/or identify analytes 130, 230, 330 without using fluorescent or radioactive labels is advantageous.

The following detailed description contains numerous specific details in order to provide a more thorough understanding of the disclosed embodiments of the invention. However, it will be apparent to those skilled in the art that the embodiments of the invention may be practiced without these specific details. In other instances, devices, methods, procedures, and individual components that are well known in the art have not been described in detail herein.

Nanotechnology is considered by some to be a field of science whose goal is to control individual atoms and molecules to create computer chips and other devices that are thousands of times smaller than current technologies permit. Current manufacturing processes use lithography to imprint circuits on semiconductor materials. While lithography has improved dramatically over the last two decades—to the point where some manufacturing plants can produce circuits smaller than one micron (1,000 nanometers)—it still deals with aggregates of millions of atoms. It is widely believed that lithography is quickly approaching its physical limits. To continue reducing the size of semiconductors, new technologies that juggle individual atoms will be necessary. This is the realm of nanotechnology. In the popular press, the term nanotechnology is sometimes used to refer to any sub-micron process, including lithography. Because of this, many scientists are beginning to use the term molecular nanotechnology when talking about true nanotechnology at the molecular level.

Cantilevers

Certain embodiments of the invention concern methods and apparatus 100, 200, 300 for analyte 130, 230, 330 detection and/or identification, using probe molecules 120, 220, 320, 520 or analytes 130, 230, 330 attached to one or more cantilevers 110, 210, 310, 400, 510, 600, 700. A cantilever 110, 210, 310, 400, 510, 600, 700 is a small, thin elastic lever that is attached at one end 660 and free at the other end 420, 620(e.g., FIG. 4, FIG. 5 and FIG. 6). Typically, probe molecules 120, 220, 320, 520 are attached to a cantilever 110, 210, 310, 400, 510, 630 surface and allowed to bind to one or more target analytes 130, 230, 330. Alternatively, target analytes 130, 230, 330 may be attached to a cantilever 110, 210, 310, 400, 510, 630 surface and allowed to bind to one or more probes 120, 220, 320, 520. One or more probe molecules 120, 220, 320, 520 or target analytes 130, 230, 330 may be attached to each cantilever 110, 210, 310, 400, 510, 630. In various embodiments, cantilevers 110, 210, 310, 400, 510, 600, 700 may be nanoscale or microscale cantilevers 110, 210, 310, 400, 510, 600, 700.

Techniques for fabrication of microscale or nanoscale cantilevers 110, 210, 310, 400, 510 or cantilever arrays 500 are known. (E.g., Baller et al., *Ultramicroscopy.* 82:1–9, 2000; Lang et al., *Appl. Phys. Lett.* 72:383, 1998; Lang et al., *Analytica Chimica Acta* 393:59, 1999; Hansen et al., *Anal. Chem.* 73:1567–71, 2001; Wu et al., *Proc. Natl. Acad. Sci. USA* 98:1560–64, 2001; Fritz et al., 2000; Ilic et al., *Appl. Phys. Lett.* 77:450–452, 2000; U.S. Pat. Nos. 6,074,484; 6,079,255; see also the world wide web at: http://monet-.physik.unibas.ch/nose/inficon/; http://www.phantomsnet-.com/phantom/net/phantomsconf/doc/Abadal.pdf; http://lmn.web.psi.ch/annrep/mntech3.pdf; http://www.nnf.cornell.edu/2001cnfra/200138.pdf; http://www.princeton.edu/~cml/html/research/biosensor.html).

Any such known fabrication method may be used in the practice of the claimed subject matter. Cantilevers 110, 210, 310, 400, 510 known in the field of atomic force microscopy are typically about 100 to 500 micrometers (μm) long and about 1 μm thick. Silicon dioxide cantilevers 110, 210, 310, 400, 510, 600, 700 varying from 15 to 500 μm in length, 5 to 50 μm in width and 320 nanometers (nm) in thickness, that were capable of detecting binding of single *E. coli* cells, have been manufactured by known methods (Ilic et al., *Appl. Phys. Lett.* 77:450, 2000). The material is not limiting, and any other material known for cantilever 110, 210, 310, 400, 510, 600, 700 construction, such as silicon or silicon nitride may be used. In other embodiments of the invention, cantilevers 110, 210, 310, 400, 510 of about 50 μm length, 10 μm width and 100 nm thickness may be used. In certain embodiments of the invention, nanoscale cantilevers 110, 210, 310, 400, 510 as small as 100 nm in length may be used. In some embodiments, cantilevers 110, 210, 310, 400, 510 of between about 10 to 500 μm in length, 1 to 100 μm in width and 100 nm to 1 μm in thickness may be used.

In various embodiments of the invention, the forces on the cantilever 110, 210, 310, 400, 510, 600, 700 may be balanced to maintain the cantilever 110, 210, 310, 400, 510, 600 in a fixed position. Where the surface of the cantilever 110, 210, 310, 400, 510, 630 is attached to one or more probe molecules 120, 220, 320, 520, binding of a target analyte 130, 230, 330 to a probe molecule 120, 220, 320, 520 may cause a change in the initial force applied to the cantilever 110, 210, 310, 400, 510, resulting in bending or deflection of the cantilever 110, 210, 310, 400, 510. A second, counterbalancing force may be applied to the cantilever 110, 210, 310, 400, 510, 610 to restore the cantilever 110, 210, 310, 400, 510, 600, 700 to its initial position. Deflection of the cantilever 110, 210, 310, 400, 510, 680 may be detected, for example, by a detection unit operably coupled to a computer. The computer may regulate the application of a second, counterbalancing force 610, creating a feedback loop that maintains the cantilever 110, 210, 310, 400, 510, 600, 700 in a fixed position. Methods and apparatus 100, 200, 300 for using feedback loops to control cantilever 110, 210, 310, 400, 510 position are generally known, for example in the field of atomic force microscopy.

Figure 2:
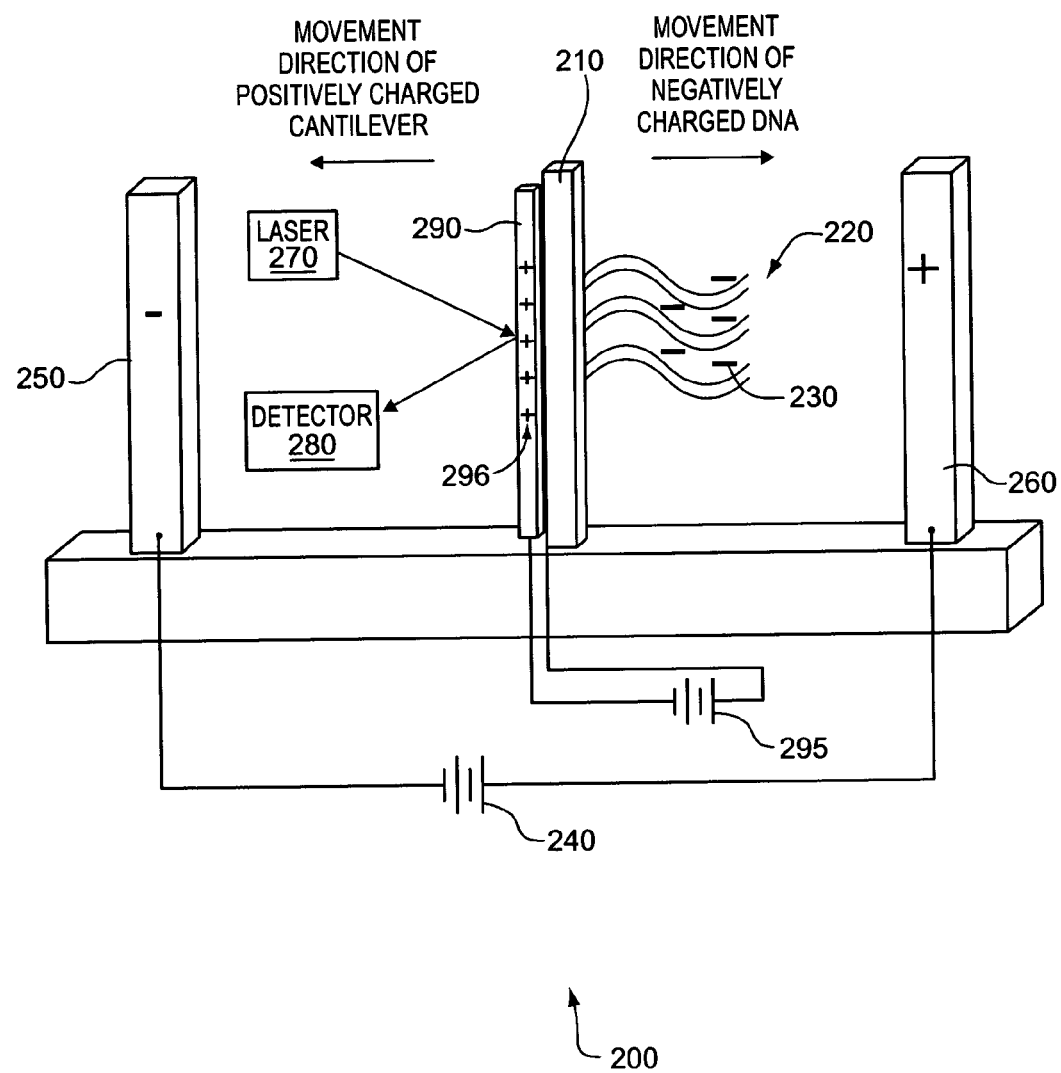
FIG. 2 illustrates an exemplary apparatus 200 (not to scale) for analyte 230 detection using a charge-balanced cantilever 210 system.
Figure 3:
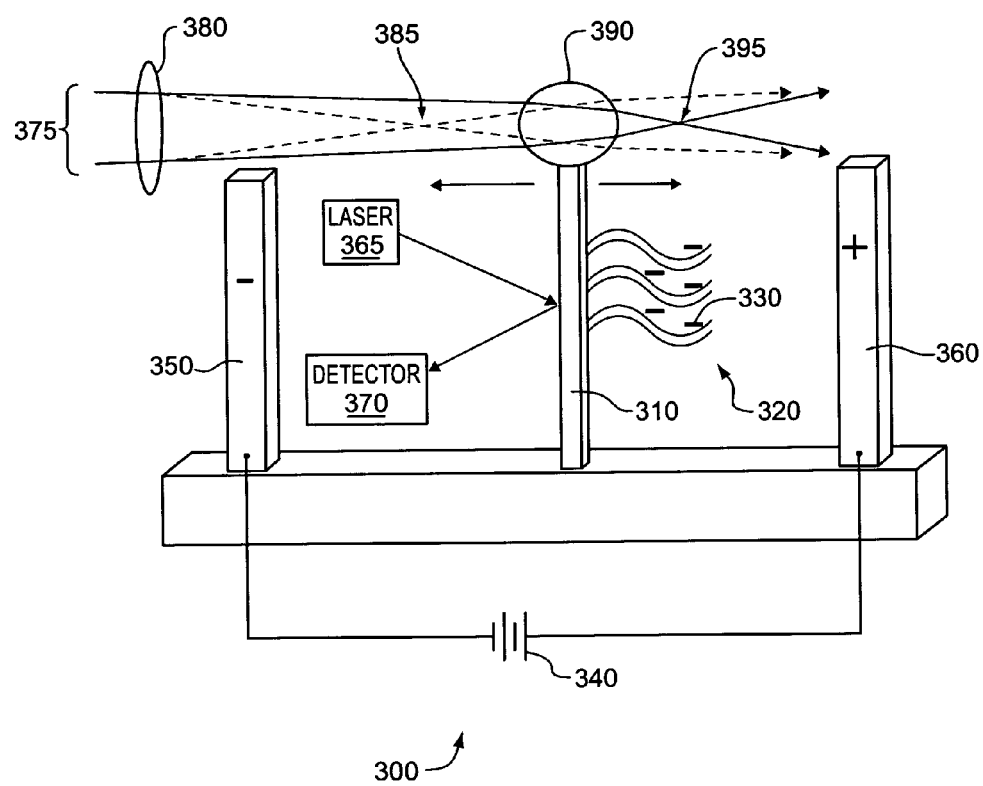
FIG. 3 illustrates an exemplary apparatus 300 (not to scale) for analyte 330 detection using a radiation pressure-balanced cantilever 310 system.

In particular embodiments of the invention, probe molecules 120, 220, 320, 520 attached to the cantilever 110, 210, 310, 400, 510, 600, 700 surface may bind to a charged target analyte 130, 230, 330 (FIG. 1 through FIG. 3). In the presence of an externally imposed electrical field, binding of charged target analytes 130, 230, 330 to probes 120, 220, 320, 520 attached to the cantilever 110, 210, 310, 400, 510, 600, 700 will result in an initial force applied to the cantilever 110, 210, 310, 400, 510 that will tend to deflect the cantilever 110, 210, 310, 400, 510, 690 from a fixed (neutral) position. Imposition of a second, counterbalancing force 695, 795 may be used to return the cantilever 110, 210, 310, 400, 510, 600 to its original position. In various embodiments, the counterbalancing force may be magnetic (FIG. 1), electrical/heater (FIG. 2, FIG. 6), or electromagnetic radiation (FIG. 3). The skilled artisan will realize that the charge on certain analytes 130, 230, 330, such as proteins, may vary depending on the pH of the solution. Manipulation of pH to maintain an appropriate charge on an analyte 130, 230, 330 is well within the skill in the art. In various embodiments of the invention, the charge on an analyte 130, 230, 330 may also be manipulated by covalent modification of the analyte 130, 230, 330, for example by introduction of charged groups. Such variations should be made without affecting the ability of the analyte 130, 230, 330 to bind to a probe molecule 120, 220, 320, 520.

The skilled artisan will realize that binding of analyte 130, 230, 330 to a cantilever 110, 210, 310, 400, 510 does not necessarily have to result in a change in surface charge of the cantilever 110, 210, 310, 400, 510, 600, 700 in order to initiate deflection. In other embodiments of the invention, binding of analyte 130, 230, 330 or probe 120, 220, 320, 520 to the cantilever 110, 210, 310, 400, 510, 600 surface may effect a deflection due to a change in surface tension. In such case, the cantilever 110, 210, 310, 400, 510, 600, 700 may still be subjected to a magnetic, electrical or radiative counterbalancing force 610 to return it to its original position. Thus, binding of either charged or uncharged analytes 130, 230, 330 may be detected using the disclosed apparatus 100, 200, 300 and methods.

In certain embodiments of the invention, the concentration of analyte 130, 230, 330 molecules in a sample may be determined by the magnitude of the second, counterbalancing force that is required to maintain the cantilever 110, 210, 310, 400, 510 in a fixed (neutral) position. One advantage of restoring the cantilever to its neutral position is because these cantilevers 110, 210, 310, 400, 510, 600, 700 have a greater dynamic range of analyte 130, 230, 330 concentrations that may be determined than with methods that measure the degree of cantilever 110, 210, 310, 400, 510, 600, 700 deflection upon analyte 130, 230, 330 binding. Also, because the cantilever 110, 210, 310, 400, 510, 600, 700 is maintained in a fixed position, the lifetime of the cantilever 110, 210, 310, 400, 510, 600, 700 is much greater than cantilevers 110, 210, 310, 400, 510, 600, 700 that undergo repetitive bending that can result in mechanical stress and structural failure.

The position of the cantilever 110, 210, 310, 400, 510, 600, 700 may be determined by any method known in the art (e.g. U.S. Pat. Nos. 6,079,255 and 6,033,852), such as using a detection unit to monitor the position of the cantilever 110, 210, 310, 400, 510, 600, 700. In some embodiments, the detection unit may comprise a signal source, such as a laser 170, 270, 365, 540, operably coupled to a photodetector 180, 280, 370, 550. Alternatively, a piezoelectric sensor attached to or incorporated into the cantilever 110, 210, 310, 400, 510, 600, 700 may be operably coupled to a detector 180, 280, 370, 550 or directly coupled to a data processing and control unit. In an exemplary embodiment of the invention, a low power laser beam may be focused on a surface of a cantilever 110, 210, 310, 400, 510, 600, 700. The laser beam may reflect off the cantilever 110, 210, 310, 400, 510 670, 680 surface to strike a position sensitive photodetector 180, 280, 370, 550 (PSD). When the cantilever 110, 210, 310, 400, 510, 600, 700 bends in response to binding of a probe 120, 220, 320, 520 or target analyte 130, 230, 330, the position that the reflected laser beam strikes the PSD 180, 280, 370, 550 moves, generating a deflection signal 680, 780. The degree of deflection of the cantilever 110, 210, 310, 400, 510, 600, 700 may be determined from the amount of displacement of the reflected laser beam on the PSD 180, 280, 370, 550, 680. Return of the cantilever 110, 210, 310, 400, 510, 600 to its initial position 695, 795 by imposition of a counterbalancing force 610, 710 may be detected by the return of the reflected laser beam to its initial position on the PSD 180, 280, 370, 550, 695, 795. The skilled artisan will realize that many different types of sensors and control systems may be used to balance the cantilever 110, 210, 310, 400, 510, 600, 700 position and any of these may be used in the practice of the claimed subject matter.

Figure 6:
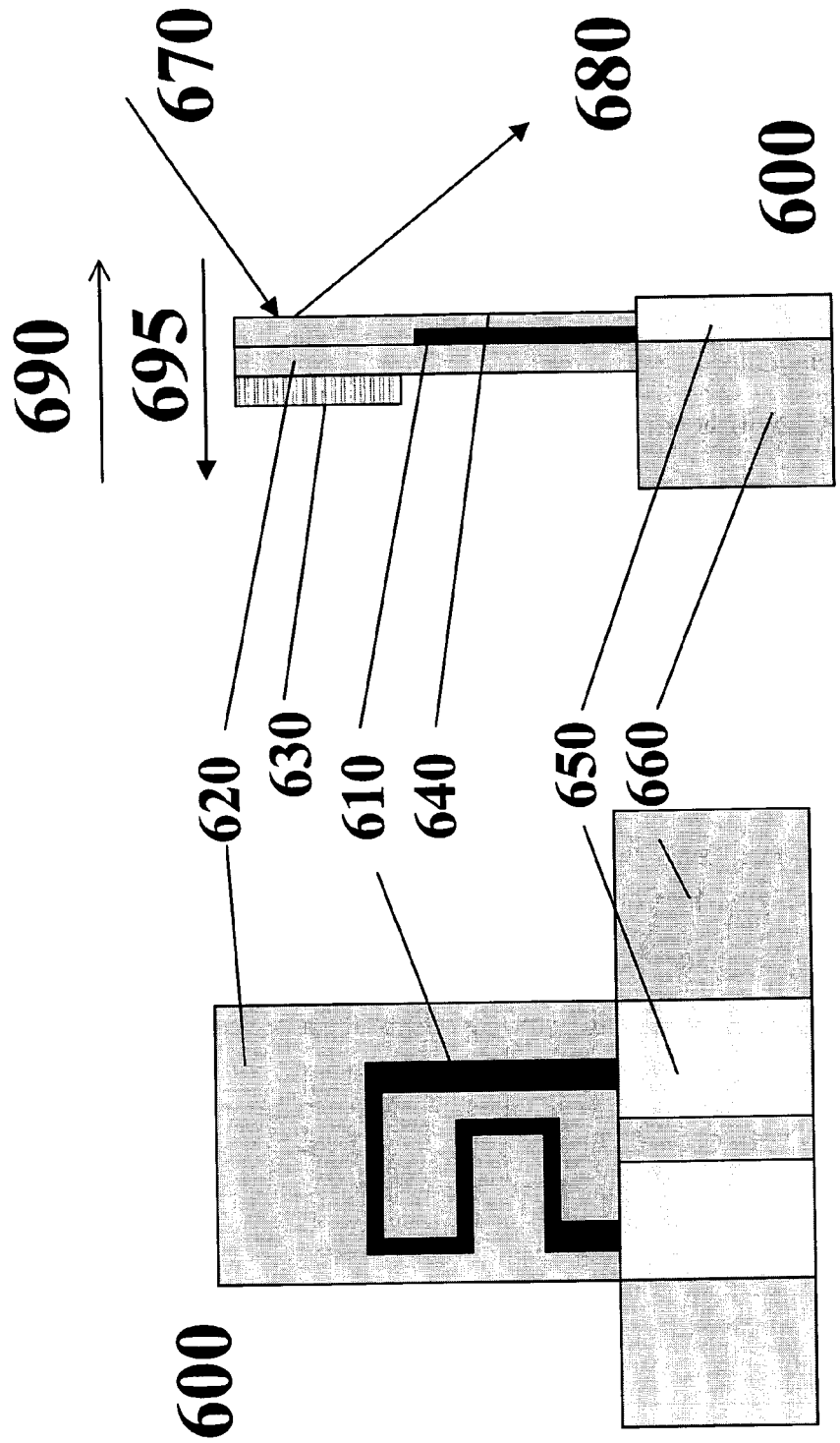
FIG. 6 illustrates an exemplary cantilever 600 including a heater (610) (not to scale).

In one embodiment, the cantilever may include a heater 610, 710 as illustrated in FIG. 6 and FIG. 7. The general structure of the cantilever may have 4 components: (1) body of the cantilever 620, 720, that may be made up of standard material, such as silicon; (2) heater 610, 710 that is likely made of metal with relatively high resistance; (3) insulation layer 640, 740 that is for example non-conductive and used to protect the heater; and (4) at least one binding surface 630, 730 (functionalized surface), this for example may be on the opposite site of the heater.

In one embodiment, the cantilever may include a heater oriented in a specific way for example horizontally symmetric as illustrated (FIG. 7). This will alleviate any torsional distortion that may be created by a heater oriented in another way. In addition, one modification to the cantilever 700 itself may be to coat the cantilever with more than one substance. It is known that a silicon-coated surface alone may not reach the correct temperature to bend the cantilever. The thermal expansion coefficient of silicon is only 2.6e-6/K (at room temperature) therefore it may not get enough heat to cause the cantilever to bend back to its original position. Thus, one consideration for coating the cantilever surface to allow heating may be to use a combination of substances such as bimetal or silicon and a metal substance. Any combination of materials with large differences of coefficient of thermal expansion between the top and the bottom substance may work. A bimorph substance such as a bimetal will allow the thermal bending to occur. A bimetal may be generated by adjoining two metals of different thermal expansion coefficients, such as invar and copper. In one embodiment, a bimetal such as invar and copper may be used to coat the cantilever and the heater 710 may be placed either on one side of the cantilever or may be placed between the two bimetallic materials.

In one example when analyte molecules bind to the binding surface 630, 730 the cantilever will bend towards the back of the binding surface 690, 790 due to surface tension stress. The bending can be detected by monitoring light reflection from the cantilever 670, 680, 770, 780. The bending force can be counter-balanced by heating the cantilever through the electrical heater 610, 710. The temperature of the cantilever may be measured by monitoring the resistance change of the heater. Temperature of the cantilever may be regulated by controlling the current 650, 750 that passes through or voltage that is applied to the heater. There may be a feedback loop between the optical detector and the heater controller. The optical-electrical control system may be made by standard electrical engineering methods. In one example, the heater 610, 710 and binding area 630, 730 may not overlap so that a temperature change will not affect analyte binding to the cantilever 600, 700. Bending force created by the heater 610, 710 may be calibrated with the optical detector.

In one example, fabrication of cantilever may include standard procedures known in the art to fabricate the main body of the cantilever 620, 720. To create the heater 610, 710, a thin layer (10 nm) of Titanium (Ti) may be deposited on one side of the cantilever. On top of the Ti layer, a thin layer of gold with specific pattern may be deposited to ensure sufficient resistance when a voltage is applied. The insulation layer may be silicon that is used to prevent electrolysis. The insulation layer 640, 740 may be thinner (eg. 50 nm) than the body structure of the cantilever 620, 720 (eg. 500 nm). Optionally a thin metal layer may be deposited outside the insulation layer 640, 740. The metal layer may provide two functions, (1) to make it more difficult to be functionalized when compared to the other side of the cantilever; and (2) to allow the heat to be more evenly distributed.

In one exemplary method the cantilever 600, 700 may be functionalized by treating the silicon side of the cantilever with, for example oxygen plasma, to create a thin silicon oxide layer. After this treatment, the cantilever 600, 700 may be functionalized using silanizing reagent following standard procedure known in the art (see also the world wide web at: cgr.harvard.edu/macbeath/research/sm_microarrays/sm_microarrays.html). The linker group to be used for probe (antibody or receptor) attachment may for example include amine, aldehyde, carboxyl, thiol, or hydroxyl group(s).

In certain embodiments of the invention the quantity of probe molecules 120, 220, 320, 520 or target analytes 130, 230, 330 bound to a cantilever 110, 210, 310, 400, 510, 600, 700 may be limited. In other embodiments of the invention, probe molecules 120, 220, 320, 520 may be attached to one or more cantilevers 110, 210, 310, 400, 510, 600, 700 in particular patterns and/or orientations to obtain an optimized signal. The patterning of the probe molecules 120, 220, 320, 520 or analytes 130, 230, 330 may be achieved by coating the surface with various known functional groups (e.g., Baller et al., 2000). Patterning may also be achieved using a photolithographic method. Photomasks may be used to protect or expose selected areas of a surface to a light beam. The light beam activates the chemistry of a particular area, allowing attachment of probe molecules 120, 220, 320, 520 or target analytes 130, 230, 330 to activated regions and not to protected regions. Photolithographic methods are known in the art. In other alternative embodiments, probe molecules 120, 220, 320, 520 may be printed onto the cantilever 110, 210, 310, 400, 510, 600, 700 surfaces by known inkjet printing methods. In some cases, probe molecules 120, 220, 320, 520 may be delivered to cantilever 110, 210, 310, 400, 510, 600, 700 supporting structures and the probe molecules 120, 220, 320, 520 may migrate onto the cantilever 110, 210, 310, 400, 510, 600, 700 surfaces by capillary action.

Detection Units

A detection unit may be used to detect the deflection of a cantilever 110, 210, 310, 400, 510, 600, 700. The deflection of a cantilever 110, 210, 310, 400, 510, 600, 700 may be detected, for example, using optical and/or piezoresistive detectors 170, 270, 365, 540 (e.g., U.S. Pat. No. 6,079,255) and/or surface stress detectors 170, 270, 365, 540 (e.g. Fritz et al., Science 288:316–8, 2000).

Piezoresistive Detectors

In an exemplary embodiment of the invention, a piezoresistive detector 180, 280, 370, 550 may be embedded at the fixed end of a cantilever 110, 210, 310, 400, 510, 600, 700 arm 410. Deflection of the free end 420, 620 of the cantilever 110, 210, 310, 400, 510, 600 produces stress along the cantilever 110, 210, 310, 400, 510, 600, 700. The stress changes the resistance of the detector 180, 280, 370, 550 in proportion to the degree of cantilever 110, 210, 310, 400, 510, 600, 700 deflection. A resistance measuring device may be coupled to the piezoresistive detector 180, 280, 370, 550 to measure its resistance and to generate a signal corresponding to the cantilever 110, 210, 310, 400, 510, 600, 700 deflection. By interfacing the detector 180, 280, 370, 550 with an information processing and control system, the degree of cantilever 110, 210, 310, 400, 510, 600, 700 deflection may be determined and used to calculate the amount of counterbalancing force 695, 795 required to return the cantilever 110, 210, 310, 400, 510, 60, 7000 to its original position. Piezoresistive detectors 170, 270, 365, 540 may be formed in a constriction at the fixed end of the cantilever 110, 210, 310, 400, 510, 600 such that the detector 180, 280, 370, 550 undergoes even greater stress when the cantilever 110, 210, 310, 400, 510, 600, 700 is deflected (PCT patent application WO97/09584).

In a non-limiting example, piezoresistive cantilevers 110, 210, 310, 400, 510, 600, 700 may be formed by defining one or more cantilever 110, 210, 310, 400, 510, 600, 700 shapes on the top layer of a silicon-on-insulator (SOI) wafer. The cantilever 110, 210, 310, 400, 510, 600 may be doped with boron or another dopant to create a p-type conducting layer. A metal may be deposited for electrical contacts to the doped layer, and the cantilever 110, 210, 310, 400, 510, 600, 700 is released by removing the bulk silicon underneath it. Such methods may use known lithography and etching techniques.

In alternative embodiments of the invention, a thin oxide layer may be grown after dopant introduction to reduce the noise inherent in the piezoresistor. Piezoresistor cantilevers 110, 210, 310, 400, 510, 600, 700 may also be grown by vapor phase epitaxy using known techniques. In certain embodiments of the invention, by incorporating the piezoresistor into a Wheatstone bridge circuit with reference resistors, the resistivity of the cantilever 110, 210, 310, 400, 510, 600, 700 may be monitored.

Optical Detectors

In other embodiments of the invention, cantilever 110, 210, 310, 400, 510, 600, 700 deflection may be detected using an optical detection unit. An optical detection unit may comprise a light source, e.g. a laser diode 170, 270, 365, 540 or an array of vertical cavity surface emitting lasers 170, 270, 365, 540 (VCSEL), and one or more position sensitive photodetectors 180, 280, 370, 550. A preamplifier may be used to convert the photocurrents into voltages. The light emitted by the light source 170, 270, 365, 540 is directed onto a surface of the cantilever 110, 210, 310, 400, 510, 600, 700 and reflected to one or more photodiodes 180, 280, 370, 550. In certain embodiments of the invention, a portion of the cantilever 110, 210, 310, 400, 510, 600, 700 may be coated with a highly reflective surface, such as silver, to increase the intensity of the reflected beam. Deflection of the cantilever 110, 210, 310, 400, 510, 600, 700 leads to a change in the position of the reflected light beams. This change can be detected by the position sensitive photodetector 180, 280, 370, 550 and analyzed to determine the deflection of the cantilever 110, 210, 310, 400, 510, 600, 700. The displacement of the cantilever 110, 210, 310, 400, 510, 600, 700 in turn may be used to determine the amount of counterbalancing force required to restore the cantilever 110, 210, 310, 400, 510, 600, 700 to its initial position.

Other Detectors

In other embodiments of the invention, deflection of the cantilever 110, 210, 310, 400, 510, 600, 700 may be measured using piezoelectric (PE) and/or piezomagnetic detection units (e.g., Ballato, "Modeling piezoelectric and piezomagnetic devices and structures via equivalent networks," *IEEE Trans. Ultrason. Ferroelectr. Freq. Control* 48:1189–240, 2001). Piezoelectric detection units utilize the piezoelectric effects of the sensing element(s) to produce a charge output. A PE detection unit does not require an external power source for operation. The "spring" sensing elements generate a given number of electrons proportional to the amount of applied stress. Many natural and man-made materials, such as crystals, ceramics and a few polymers display this characteristic. These materials have a regular crystalline molecular structure, with a net charge distribution that changes when strained.

Piezoelectric materials may also have a dipole in their unstressed state. In such materials, electrical fields may be generated by deformation from stress, causing a piezoelectric response. Charges are actually not generated, but rather are displaced. When an electric field is generated along the direction of the dipole, mobile electrons are produced that move from one end of the piezoelectric material, through a signal detector 180, 280, 370, 550 to the other end of the piezoelectric material to close the circuit. The quantity of electrons moved is a function of the degree of stress in the piezoelectric material and the capacitance of the system.

The skilled artisan will realize that the detection techniques discussed herein are exemplary only and that any known technique for detecting deflection of a cantilever 110, 210, 310, 400, 510, 600, 700 may be used.

Micro-Electro-Mechanical Systems (MEMS)

In some embodiments of the invention, one or more cantilevers 110, 210, 310, 400, 510, 600, 700 may be incorporated into a Micro-Electro-Mechanical System (MEMS). MEMS are integrated systems comprising mechanical elements, sensors, actuators, and electronics. All of those components may be manufactured by known microfabrication techniques on a common chip, comprising a silicon-based or equivalent substrate (e.g., Voldman et al., *Ann. Rev. Biomed. Eng.* 1:401–425, 1999). The sensor components of MEMS may be used to measure mechanical, thermal, biological, chemical, optical and/or magnetic phenomena. The electronics may process the information from the sensors and control actuator components such pumps, valves, heaters, coolers, filters, etc. thereby controlling the function of the MEMS. In an exemplary embodiment of the invention, a sensor component may measure deflection of one or more cantilevers 110, 210, 310, 400, 510, 600, 700, while control actuator elements may expose the cantilevers 110, 210, 310, 400, 510, 600, 700 to sample solutions or to provide a counterbalancing force to maintain the cantilevers 110, 210, 310, 400, 510, 600, 700 in a fixed position. In another exemplary embodiment, a cantilever 110, 210, 310, 400, 510, 600, 700 or cantilever array 500 may be contained in a fluid chamber. Various pumps, valves and other actuators may be used to control the entry of samples into the fluid chamber and exit of fluids from the chamber. An exemplary MEMS device may also comprise a laser 170, 270, 365, 540, photodetector 180, 280, 370, 550 and other electronic elements, such as power supplies 140, 195, 240, 295, 340, 560 and electrodes 150, 160, 250, 260, 350, 360.

The electronic components of MEMS may be fabricated using integrated circuit (IC) processes (e.g., CMOS, Bipolar, or BICMOS processes). They may be patterned using photolithographic and etching methods known for computer chip manufacture. The micromechanical components may be fabricated using micromachining processes that selectively etch away parts of the silicon wafer or add new structural layers to form the mechanical and/or electromechanical components. Basic techniques in MEMS manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrochemical deposition, chemical deposition, electroplating, thermal diffusion and evaporation, physical vapor deposition, sol-gel deposition, electrodeposition, epitaxy and thermal oxidation and physical procedures like physical vapor deposition (PVD) and casting.

The manufacturing method is not limiting and any methods known in the art may be used, such as laser ablation, injection molding, molecular beam epitaxy, dip-pen nanolithograpy, reactive-ion beam etching, chemically assisted ion beam etching, microwave assisted plasma etching, focused ion beam milling, electro-oxidation, scanning probe methods, chemical etching, electron beam or focused ion beam technology or imprinting techniques (e.g., U.S. Pat. No. 6,146,227; see also the world wide web at: mdatechnology.net/techsearch.asp?articleid=510; Bloch et al., "Optics with an atom laser beam," *Phys. Rev. Lett.* 87:123–321, 2001; Ivanisevic et al., "Dip-Pen Nanolithography on Semiconductor Surfaces," *J. Am. Chem. Soc.,* 123: 7887–7889, 2001; Siegel, "Ion Beam Lithography," VLSI Electronics, Microstructure Science, Vol. 16, Einspruch and Watts eds., Academic Press, New York, 1987). Methods for manufacture of nanoelectromechanical systems may be used for certain embodiments of the invention. (e.g., Craighead, *Science* 290:1532–36, 2000.) Various forms of microfabricated chips are commercially available from, e.g., Caliper Technologies Inc. (Mountain View, Calif.) and ACLARA BioSciences Inc. (Mountain View, Calif.). Any type of known material may be used for construction of MEMS devices, including but not limited to glass, plastic, ceramic, silicon, silicon oxide, silicon dioxide, silicon nitride, germanium, gallinium arsenide, and metal-based compositions such as metals and/or metal oxides.

In various embodiments of the invention, it is contemplated that some or all of the components of an apparatus 100, 200, 300 exemplified in FIG. 1 through FIG. 7 may be constructed as part of an integrated MEMS device Applications In one embodiment the previously illustrated methods may be used to detect nucleic acids (DNA, mRNA, RNA, PNA) of infectious agents. Specific nucleic acid probes may be designed and synthesized based by procedures known in the art. For example, an amine modified DNA oligo probes can be immobilized on the surface of a cantilever functionalized with carboxyl group (linker group) using EDC chemistry (Benson et al, *Science,* 193, (2001), 1641–1644). Before detection, nucleic acids are extracted from a sample, fragmented into an average size of approximately 200 nt by DNase digestion (for example, 0.01 unit/ul DNase, in TE buffer, 37° C. for 30 min, followed by heat inactivation at 95° C. for 10 min) or for example mechanical shearing. The sample may be diluted in a buffer containing 200 mM NaCl, 10 mM Tris HCl, pH 7.8, 1 mM EDTA, plus 1 ug/ml yeast tRNA.\The sample may then be denatured by heating the DNA sample to 95° C. for 15 min. The sample may then be cooled to 4° C. before exposing it to a cantilever. Then the cantilever with sample is heated to approximately 45° C. for hybridization. After washing the cantilever with a buffer containing 100 mM NaCl, 10 mM Tris HCl, pH 7.8, 1 mM EDTA, plus 1 ug/ml yeast tRNA. Because the system may be pre-calibrated, the amount of binding material (DNA target molecules) on the cantilever may be determined by the amount of power needed to counter-balance the bending force generated from nucleic acid binding.

In another embodiment, the previously illustrated examples may be used for protein detection. For example, antibodies may be immobilized on the cantilever by the same EDC chemistry detailed in the previous example due to the large number of amine groups on an antibody's surface. In one example, a protein sample of a patient's blood may be diluted (eg. 1×PBS plus 0.1% Tween-20). After binding proteins (antigens) to the cantilever surface and washing away non-specific binding materials, specific binding may be detected by method describe above.

In another embodiment, the previously illustrated examples may be used to detect a specific cell and/or virus: Procedures similar to protein detection (illustrated previously) may be used when specific antibodies are available. Cancer cells may be detected by measuring cell surface antigen interaction (eg. tumor antigen) with immobilized antibodies on the cantilevers.

In another embodiment, the previously illustrated examples may be used to detect a specific one or more ligands and/or ligand-receptors (eg. ligand proteins). For example ligand receptors may be immobilized on cantilevers using the EDC chemistry as illustrated previously. Detection methods may be similar to those used for protein detection.

In another embodiment, the previously illustrated examples may be used to detect any other molecular interaction(s). In principle any known detector molecule(s) may be immobilized on the surface of a cantilever and methods similar to protein detection may be used to detect the binding events.

In many of the applications, real-time (instant) detection may be performed without the washing steps, meaning after exposing the cantilever to a sample, and allowing the system to stabilize, data may be collected and results may be analyzed without removal of the excess sample. For other biochemical protocols, see "Molecular Cloning: A Laboratory Manual" by Joseph Sambrook, David W. Russell, published by Cold Spring Harbor Press, N.Y.

Preparation of Probe Molecules

It is contemplated that a wide variety of probe molecules 120, 220, 320, 520 may be used in the practice of the claimed subject matter. The discussion below focuses on two types of probes 120, 220, 320, 520—oligonucleotides and antibodies—of use in various embodiments of the invention. However, the skilled artisan will realize that any type of known probe molecule 120, 220, 320, 520 may be used. Methods for preparing and using other types of probes 120, 220, 320, 520 are known in the art.

Oligonucleotide Probes

In certain embodiments of the invention, oligonucleotide probes 120, 220, 320, 520 may be used for detecting a variety of nucleic acid analytes 130, 230, 330, such as messenger ribonucleic acids (RNA), genomic deoxyribonucleic acids (DNA), cloned nucleic acid inserts, nucleic acid amplification products, or any other type of nucleic acid. Oligonucleotides 120, 220, 320, 520 may bind to nucleic acid analytes 130, 230, 330 by standard Watson-Crick base pairing, in which adenine ("A") residues hydrogen bond with thymine ("T") or uracil ("U") residues and cytosine ("C") residues hydrogen bond with guanine ("G") residues. Methods of preparing oligonucleotide probes 120, 220, 320, 520 are well known in the art. Oligonucleotides 120, 220, 320, 520 may be synthesized on commercially available synthesizers (e.g., Applied Biosystems, Foster City, Calif.) or may be purchased from commercial vendors (e.g., Midland Certified Reagents, Midland, Tex.; Proligo, Boulder, Colo.). Although standard oligonucleotides 120, 220, 320, 520 may be used, any modification or analogue of an oligonucleotide 120, 220, 320, 520, such a peptide nucleic acid 120, 220, 320, 520, may be used in the disclosed methods.

In general, oligonucleotides of at least 6, 7 or 8 bases in length may be used as probes 120, 220, 320, 520 for nucleic acid hybridization. In certain embodiments of the invention, longer oligonucleotides 120, 220, 320, 520 of 9, 10, 11, 12, 13, 14, 15, 20, 25, 30, 35, 40, 45, 50, 60, 75, 100 or longer bases may be used. The use of oligonucleotides 120, 220, 320, 520 of 13 bases or longer may facilitate specific binding to a selected target nucleic acid analyte 130, 230, 330. The skilled artisan is familiar with techniques for selecting and preparing oligonucleotide probes 120, 220, 320, 520 that will bind specifically to a target nucleic acid analyte 130, 230, 330, such as performing computer database searches for unique portions of a target nucleic acid sequence. In various embodiments of the invention, oligonucleotide probes 120, 220, 320, 520 may be prepared that exhibit selective or specific binding to a given target sequence.

Oligonucleotides 120, 220, 320, 520 may be hybridized to target nucleic acids 130, 230, 330 using varying degrees of stringency. Applications requiring high selectivity will typically employ relatively stringent conditions to form the hybrids, e.g., relatively low salt and/or high temperature conditions, such as about 0.02 M to about 0.10 M NaCl at temperatures of about 50° C. to about 70° C. Such high stringency conditions tolerate little, if any, mismatch between the probe 120, 220, 320, 520 and the target strand 130, 230, 330, and would be particularly suitable for detecting specific nucleic acid targets. Alternatively, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. It is generally appreciated that conditions can be rendered more stringent by the addition of increasing amounts of formamide.

In certain embodiments of the invention, the rate or efficiency of probe 120, 220, 320, 520 binding to analytes 130, 230, 330 may be increased by using focused electrical fields to move and concentrate charged analytes 130, 230, 330 in the vicinity of the cantilevers 110, 210, 310, 400, 510. In some cases, the stringency of probe 120, 220, 320, 520 hybridization to analytes 130, 230, 330 may also be electronically controlled. Methods and apparatus 100, 200, 300 for controlling analyte 130, 230, 330 movement and hybridization are known in the art (e.g., U.S. Pat. Nos. 6,051,380 and 6,207,373)

Antibody Probes

Methods for preparing and using antibody probes 120, 220, 320, 520 are well known in the art (e.g., Harlow and Lane, *Antibodies: A Laboratory Manual*, Cold Spring Harbor Laboratory, 1988). Antibodies 120, 220, 320, 520 may be either polyclonal or monoclonal. To generate polyclonal antibodies 120, 220, 320, 520, an antigen of interest is injected into a subject animal, such as a rabbit. The reactivity of the antigen may be increased by co-administering adjuvants, such as Freund's complete or incomplete adjuvant. Antigenicity may be increased by attaching the antigen to a carrier, such as bovine serum albumin or keyhole limpet hemocyanin. The immune response of the animal may be increased by periodically administering a booster injection of the antigen. Antibodies 120, 220, 320, 520 are secreted into the circulation of the animal and may be obtained by bleeding or cardiac puncture. Antibodies 120, 220, 320, 520 may be separated from other blood components by well-known methods, such as blood clotting, centrifugation, filtration and/or immunoaffinity purification (e.g., using anti-rabbit antibodies) or affinity chromatography (e.g., Protein-A Sepharose column chromatography).

Monoclonal antibodies 120, 220, 320, 520 (MAbs) may be prepared through use of well-known techniques, such as those exemplified in U.S. Pat. No. 4,196,265. Typically, the technique involves immunizing a suitable animal, such as a mouse, with an antigen. Carriers and/or adjuvants as disclosed above may be used, along with periodic administration of booster injections. Antibody-producing B cells are obtained from an immunized animal, for example by removing the spleen or lymph nodes and purifying lymphocytes. These are fused with immortalized cells of a myeloma cell line to generate antibody-producing hybridoma cells. Such cells secrete antibodies 120, 220, 320, 520 into the medium that may be further purified as discussed above. Individual hybridoma clones secreting a single type of antibody 120, 220, 320, 520 may be obtained by serial dilution and cell culture. The selectivity of different antibody 120, 220, 320, 520 clones for a given target analyte 130, 230, 330 may be determined by standard methods, such as Western blotting.

In various embodiments of the invention, antibody fragments 120, 220, 320, 520, such as FAb fragments 120, 220, 320, 520, may be prepared by known methods and used as probes 120, 220, 320, 520. Methods are known for preparing modified antibodies 120, 220, 320, 520, genetically engineered antibodies 120, 220, 320, 520, humanized antibodies 120, 220, 320, 520 and/or single-chain antibodies 120, 220, 320, 520. Any such antibody, antibody fragment or antibody analogue may be used as a probe molecule 120, 220, 320, 520.

Attachment of Probe Molecules or Target Analytes to Surfaces

In various embodiments of the invention, probe molecules 120, 220, 320, 520 or target analytes 130, 230, 330 may be attached to the surface of one or more cantilevers 110, 210, 310, 400, 510. Methods for attaching various types of molecules to surfaces are well known in the art. The following exemplary embodiments of the invention are presented for illustrative purposes only and are not limiting for the scope of the claimed subject matter.

In various embodiments of the invention, probe molecules 120, 220, 320, 520 or analytes 130, 230, 330 of interest may be attached to a surface by covalent or non-covalent interaction. In a non-limiting example, attachment may occur by coating a surface with streptavidin or avidin and then binding of biotinylated probe molecules 120, 220, 320, 520 or target analytes 130, 230, 330. Alternatively, attachment may occur by coating a silicon or other surface with poly-L-Lys (lysine) followed by covalent attachment of either amino- or sulfhydryl-containing probe molecules 120, 220, 320, 520 or target analytes 130, 230, 330 using bifunctional crosslinking reagents (Running et al., *BioTechniques* 8:276–277, 1990; Newton et al., *Nucleic Acids Res.* 21:1155–62, 1993). The skilled artisan will realize that alternative attachment techniques could be used, such as direct covalent bonding of carboxyl-containing probes 120, 220, 320, 520 or analytes 130, 230, 330 to the lysine amino side chains, for example by using a carbodiimide cross-linking reagent.

In other embodiments of the invention, probe molecules 120, 220, 320, 520 or target analytes 130, 230, 330 may be attached to a surface using photopolymers that contain photoreactive species such as nitrenes, carbenes or ketyl radicals (See U.S. Pat. Nos. 5,405,766 and 5,986,076). Attachment may also occur by coating the surface with derivatized metals, followed by covalent attachment of amino- or sulfhydryl-containing probe molecules 120, 220, 320, 520 or target analytes 130, 230, 330. Where the native probes 120, 220, 320, 520 or analytes 130, 230, 330 do not contain amino or sulfhydryl groups, the probe 120, 220, 320, 520 or analyte 130, 230, 330 may be covalently modified by known methods to include an appropriate group.

Other exemplary methods for cross-linking molecules are disclosed in U.S. Pat. No. 5,603,872 and U.S. Pat. No. 5,401,511. Various ligands can be covalently bound to surfaces through the cross-linking of amine residues. In another non-limiting example, heterobifunctional cross-linking reagents and methods of using the cross-linking reagents are disclosed in U.S. Pat. No. 5,889,155. The cross-linking reagents combine, for example, a nucleophilic hydrazide residue with an electrophilic maleimide residue, allowing coupling, in one example, of aldehydes to free thiols. The cross-linking reagent used can be designed to cross-link various functional groups.

Another technique for anchoring probes 120, 220, 320, 520 or analytes 130, 230, 330 onto a solid surface is based on self-assembling monolayers such as silanes. Such molecules may form a well ordered, densely packed monolayer that can be used to anchor probes 120, 220, 320, 520 or analytes 130, 230, 330. Amine groups may be coated on a surface through the use of aminosilane. Alternative silanes of use include 3-glycidoxypropyltrimethoxysilane (GOP) or aminopropyltrimethoxysilane (APTS). Various types of probes 120, 220, 320, 520 or analytes 130, 230, 330 may be attached to the silanes either directly or through the use of cross-linking reagents.

In embodiments of the invention involving oligonucleotide or nucleic acid probes 120, 220, 320, 520 or analytes 130, 230, 330, attachment may take place by direct covalent attachment of 5'-phosphorylated nucleic acids to chemically modified surfaces (Rasmussen et al., *Anal. Biochem.* 198: 138–142, 1991). The covalent bond between the nucleic acid and the surface may be formed, for example, by condensation with a water-soluble carbodiimide. This method facilitates a predominantly 5'-attachment of the nucleic acids via their 5'-phosphates.

Bifunctional cross-linking reagents may be of use for attachment. Exemplary cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC). In some embodiments of the invention, surface functional groups may be covalently attached to cross-linking compounds to reduce steric hindrance of the surface with probe 120, 220, 320, 520 to analyte 130, 230, 330 binding interaction. Typical cross-linking groups include ethylene glycol oligomers and diamines. The claimed methods and apparatus 100, 200, 300 are not limited to the examples disclosed herein, but may use any known method for attaching probe molecules 120, 220, 320, 520 or target analytes 130, 230, 330 to cantilevers 110, 210, 310, 400, 510.

The number of probe molecules 120, 220, 320, 520 or target analytes 130, 230, 330 to be attached to each surface will vary, depending on the sensitivity of the surface and the noise level of the system. Large cantilevers 110, 210, 310, 400, 510, 600, 700 of about 500 µm in length may utilize as many as $10^{10}$ molecules of attached probes 120, 220, 320, 520 or analytes 130, 230, 330 per cantilever 110, 210, 310, 400, 510, 600, 700. However, using smaller cantilevers 110, 210, 310, 400, 510, 600, 700 the number of attached probes 120, 220, 320, 520 or analytes 130, 230, 330 may be greatly reduced. In certain embodiments of the invention, binding of a single target analyte 130, 230, 330 to a probe molecule 120, 220, 320, 520 attached to a cantilever 110, 210, 310, 400, 510, 600, 700 may be detected by the disclosed methods.

In certain embodiments of the invention, probe molecules 120, 220, 320, 520 or analytes 130, 230, 330 may be attached to the cantilever 110, 210, 310, 400, 510, 600, 700 surface in particular patterns. Such patterns of attachment may be provided by a variety of methods known in the art. For example, a binding surface such as a gold film may be coated onto a cantilever 110, 210, 310, 400, 510, 600, 700 using known nanolithography and etching methods. Gold surfaces may be covalently attached to molecules with sulfhydryl or amine groups. Alternatively, reactive groups that are capable of binding probes 120, 220, 320, 520 or analytes 130, 230, 330 may be deposited on the surface of the cantilever 110, 210, 310, 400, 510, 600, 700 in a selected pattern using any known method, such as dip-pen nanolithography. In other alternatives, photoactivatable reactive groups may be uniformly deposited on a surface and activated in specific patterns using, for example, laser lithography.

More Applications

It is thought that physicians may test for dozens of diseases using at least one highly sensitive device that detects disease-identifying molecules by inducing them to stick to and bend a microscopic cantilever that resembles a diving board (see FIG. 1–FIG. 7). One study revealed that this technology is sensitive enough to serve as a diagnostic test for prostate-specific antigen (PSA), the protein marker characteristic of prostate cancer. In addition, the technology shows promise for finding small variations in DNA called single nucleotide polymorphisms, or SNPs (pronounced "snips"), that result in the most common forms of biological diversity.

One team of researchers (University of Southern California (USC) in Los Angeles, the University of California in Berkeley (UCB), and Oak Ridge National Laboratory (ORNL)) researched and developed a microcantilever technology. These researchers made cantilevers from silicon nitride using techniques identical to those used to make computer microprocessors. Other researchers perfected a way to coat the cantilever's top surfaces with antibodies to detect specific proteins or single-stranded DNA sequences to detect SNPs. The detailed processes of this application may be used to improve the techniques currently practiced in these laboratories by incorporating a device to restore the deflection created by analyte binding and bending of the cantilever. These improvements are needed since the higher the protein or DNA concentration that sticks to the cantilever, the greater the deflection and the greater the stress becomes on the cantilever.

In one example, a cantilever may be about 50 microns wide, (half the width of a human hair), 200 microns long (a fifth of a millimeter), and half a micron thick. In some examples, when molecules bind to the surface, the cantilever moves only about 10–20 nanometers Initial PSA test results reported that the cantilever technique is sensitive enough to detect levels 20 times lower than the clinically relevant threshold which is as good if not more sensitive than a time-consuming ELISA [enzyme-linked immunosorbent] assay, which is the standard today for detecting protein markers like PSA (prostate specific antigen).

Other markers of for example DNA mutations that predict diseases like breast cancer, colorectal cancer, and cystic fibrosis could be detected through these mismatches, even before patients exhibit symptoms. It has been observed in some case such as single-base changes that the cantilever bends up instead of down. It is envisioned that a heater placed within the cantilever as illustrated in FIG. 6 and/or FIG. 7 may also be used to reinstate the cantilever to its original position even if the cantilever bends in a different direction.

Specific Proposed Tests

Prostate-Specific Antigen

In one embodiment, the level of PSA Prostate-specific antigen may be monitored using any one or more of the methods detailed herein. PSA is produced by both normal and abnormal prostate cells. Elevated PSA levels may be found in the blood of men with benign prostate conditions, such as prostatitis (inflammation of the prostate) and benign prostatic hyperplasia (BPH), or with a malignant (cancerous) growth in the prostate. While PSA does not allow doctors to distinguish between benign prostate conditions (which are very common in older men) and cancer, an elevated PSA level may indicate that other tests are necessary to determine whether cancer is present.

PSA levels have been shown to be useful in monitoring the effectiveness of prostate cancer treatment, and in checking for recurrence after treatment has ended. In checking for recurrence, a single test may show a mildly elevated PSA level, which may not be a significant change. Physicians generally look for trends, such as steadily increasing PSA levels in multiple tests over time, rather than focusing on a single elevated result.

Coronary Heart Disease

Around 7 million Americans suffer from CHD, the most common form of heart disease. This type of heart disease is caused by a narrowing of the coronary arteries that feed the heart. CHD is the number one killer of both men and women in the U.S. Each year, more than 500,000 Americans die of heart attacks caused by CHD. The Food and Drug Administration (FDA) recently cleared for marketing a new laboratory blood test that will increase the ability of doctors to predict the risk of coronary heart disease (CHD).

The test, called PLAC, works by measuring an enzyme called lipoprotein-associated phospholipase A2. This enzyme is made by a type of white blood cell called a macrophage. Macrophages make more of this enzyme and release it into the blood when a person has CHD. In one embodiment, the level of lipoprotein-associated phospholipase A2 may be measured using a cantilever based technology of this application as one test for risk of CHD. It was discovered in one study, the greatest increased risk was found in subjects with the highest PLAC test results and LDL cholesterol levels lower than 130 mg/dL.

The PLAC test is not a definitive test for predicting CHD. The test provides supportive information when used with clinical evaluation and other tools for patient risk assessment. An elevated PLAC test result with an LDL-cholesterol level of less than 130 mg/dL provides physicians with increased confidence that patients have two to three times the risk of having coronary heart disease when compared with patients having lower PLAC test results.

Other Applications

One embodiment may include detection of exhaled nitric oxide due to the correlation of a decrease in exhaled nitric oxide concentration and the correlation that an anti-inflammatory treatment may be decreasing lung inflammation associated with asthma. Recent evidence has shown that nitric oxide levels are increased in the breath of people with asthma and that changes in nitric oxide levels may indicate whether or not treatment for asthma is working. Asthma is a highly variable disease affecting millions of people worldwide. With asthma, the lungs become inflamed and constrict, limiting airflow and making breathing difficult. The incidence of asthma in the United States has increased in recent years and it now affects about 15 million Americans, including almost five million children. Every year, asthma causes roughly 2 million emergency room visits, approximately 500,000 hospitalizations, and 4,500 deaths.

Other embodiments include screening for breast cancer for example certain genes (eg. CA 15-3, CA 549, CA M26, M29, TPA, MCA, MSA, CAM26) may be monitored, while other cancers such as ovarian cancer, CA-125 may also be monitored:

Further examples may include a rapid Strep-throat test (Group A streptococcus, Group A beta hemolytic streptococcus detection) that takes less time than the current one-hour test. Another example may be analysis of Tau/Aβ342 genes correlated in Alzheimers disease. Also, ApoE Genotyping (Apolipoprotein E genotyping) may be analyzed from a blood sample if you are suspected of also having an inherited component to your high cholesterol and triglyceride levels or other predisposing symptoms related to the diagnosis of probable Alzheimer's Disease.

In one example an array of silicon cantilevers, coated with different polymer layers was generated. Gases under analysis diffused through the different layers of polymer at different rates, causing the polymers to swell and bending the cantilevers. Examining the bending pattern of the eight cantilevers (using a technique such as neural network or principal component analysis (PCA)) provided a fingerprint for gas detection. Hans Peter Lang of IBM's Zurich Research Laboratory. Thus, these techniques have applications in process and quality control, environmental monitoring, characterizing complex odors and vapors, fragrance design, oenology (the study of wine) and in medicine, analyzing patients' breath (eg. nitric oxide as it relates to Diabetes Mellitis onset).

Diagnosis and monitoring of complex diseases such as cancer require quantitative detection of multiple proteins. An increasing number of genetic tests are becoming available as a result of recent and rapid advances in biomedical research. It has been said that genetic testing may revolutionize the way many diseases are diagnosed. But genetic testing does not just help a physician diagnose disease. There are a number of different reasons genetic tests are performed. These include the following: clinical genetic testing (diagnosing current or future disease), pharmacogenomics (assessment of therapeutic drug treatment), identity testing for criminal investigations or forensics studies (sometimes referred to as "DNA testing"), parentage testing (formerly called paternity testing), tissue typing for transplantation, cytogenetics (chromosome analysis), and infectious disease testing.

With respect to genetic testing, single nucleotide polymorphisms (SNPs) and other forms of genetic variation are the focus of intense research due to their possible role in predicting disease susceptibility and therapeutic response. Any one or more of the enclosed methods, may be used to detect the presence or absence of one or more SNP(s). (e.g. for condition or disease correlation) In addition, other types of polymorphisms (i.e., variable repeats and gene deletions) may also be assessed using the enclosed methods.

The ability of DNA and other biomolecules to operate machinery such as valves using the molecules' specific code or biochemistry may have applications in medicine. A system to attack cancerous growth: and the release of just the proper doses of chemicals in the appropriate location of the body may be achieved using tiny microcapsules equipped with nano-valves programmed chemically to open only when they get biochemical signals from a targeted tumor type. It is envisioned that cantilever technology is sensitive enough to monitor these changes. This would enable the right therapy at the right place at the right time, with minimized side effects and no invasive surgery. The method is based on directly transforming specific biochemical recognition into a nanomechanical motion.

Information Processing and Control System and Data Analysis

In certain embodiments of the invention, the cantilever 110, 210, 310, 400, 510, detection unit or other elements of the apparatus 100, 200, 300 may be interfaced with a data processing and control system. In an exemplary embodiment of the invention, the system incorporates a computer comprising a bus or other communication means for communicating information, and a processor or other processing means coupled with the bus for processing information. In one embodiment of the invention, the processor is selected from the Pentium® family of processors, including the Pentium® II family, the Pentium® III family and the Pentium® 4 family of processors available from Intel Corp. (Santa Clara, Calif.). In alternative embodiments of the invention, the processor may be a Celeron®, an Itanium®, and X-Scale or a Pentium Xeon® processor (Intel Corp., Santa Clara, Calif.). In various other embodiments of the invention, the processor may be based on Intel architecture, such as Intel IA-32 or Intel IA-64 architecture. Alternatively, other processors may be used.

The computer may further comprise a random access memory (RAM) or other dynamic storage device (main memory), coupled to the bus for storing information and instructions to be executed by the processor. Main memory may also be used for storing temporary variables or other intermediate information during execution of instructions by processor. The computer may also comprise a read only memory (ROM) and/or other static storage device coupled to the bus for storing static information and instructions for the processor. Other standard computer components, such as a display device, keyboard, mouse, modem, network card, or other components known in the art may be incorporated into the information processing and control system. The skilled artisan will appreciate that a differently equipped information processing and control system than the examples described herein may be used for certain implementations. Therefore, the configuration of the system may vary within the scope of the invention.

In particular embodiments of the invention, the detection unit may be operably coupled to the bus. A processor may process data from a detection unit. The processed and/or raw data may be stored in the main memory. The processor may analyze the data from the detection unit to determine the identity and/or quantity of target analytes 130, 230, 330 present in a sample.

The information processing and control system may further provide automated control of the cantilever 110, 210,

310, 400, 510 apparatus 100, 200, 300, such as the magnitude of counterbalancing force applied to maintain a cantilever 110, 210, 310, 400, 510 in a neutral position. Instructions from the processor may be transmitted through the bus to various output devices, for example to voltage sources, laser 170, 270, 365, 540 units, electromagnets, control pumps, electrophoretic or electro-osmotic leads and other components of the apparatus 100, 200, 300.

It should be noted that, while the processes described herein may be performed under the control of a programmed processor, in alternative embodiments of the invention, the processes may be fully or partially implemented by any programmable or hardcoded logic, such as Field Programmable Gate Arrays (FPGAs), TTL logic, or Application Specific Integrated Circuits (ASICs), for example. Additionally, the methods described may be performed by any combination of programmed general-purpose computer components and/or custom hardware components.

In certain embodiments of the invention, custom designed software packages may be used to analyze the data obtained from the detection unit. In alternative embodiments of the invention, data analysis may be performed using a data processing and control system and publicly available software packages.

EXAMPLES

Example 1

Charge-magnet Balanced Cantilever

FIG. 1 illustrates an exemplary apparatus 100 and method for analyte 130 detection and/or identification. The apparatus 100 comprises one or more cantilevers 110 attached to one or more probe molecules 120. The probe molecules 120 bind to electrically charged target analytes 130. An electrical potential gradient is imposed by a direct current power supply 140 attached to a pair of electrodes 150, 160 flanking the cantilever 110. Upon binding of a charged target analyte 130, the cantilever 110 will be deflected towards one electrode 150 or the other 160. In certain embodiments of the invention, the electrodes 150, 160 may be used to initially control movement of analytes 130 toward the probe molecules 120. After analytes 130 have bound to the probes 120, unbound analytes 130 may be moved away from the cantilever 110 (eg by washing the unbound analytes away using an appropriate buffer). Once probes 120 have bound to analytes 130, the electrodes 150, 160 may be used to impose an electrical field that causes deflection of the cantilever 110.

As discussed above, in alternative embodiments of the invention, binding of neutral analytes 130 to probe molecules 120 attached to the cantilever 110 surface may also result in deflection of the cantilever 110. The skilled artisan will realize that the same types of counterbalancing forces may be used to maintain the cantilever 110 in a neutral position, regardless of whether cantilever 110 deflection is caused by a change in surface charge or surface tension. In such embodiments, the imposition of an electrical potential gradient by a first power supply 140 as illustrated in FIG. 1 may be optional.

Deflection of the cantilever 110 may be detected by a detection unit comprising, for example, a laser 170 and a position sensitive detector 180. Light from the laser 170 is reflected off a surface of the cantilever 110 and strikes the detector 180. When the cantilever 110 bends in response to binding of an analyte 130, the position on the detector 180 at which the reflected laser beam strikes is shifted. The amount by which the reflected laser beam shifts is proportional to the degree of bending of the cantilever 110.

A counterbalancing force may be applied to return the cantilever 110 to its original fixed position. In the exemplary embodiment of the invention shown in FIG. 1, the counterbalancing force is magnetic. An electromagnet 190 may be attached to or incorporated in the cantilever 110, for example by depositing a nanowire coil on the cantilever 110 and covering the coil with an insulating material. Upon imposition of an electrical field using a second power supply 195, the nanowire coil becomes magnetized. The magnetized coil may interact, for example, with an externally imposed magnetic field gradient (not shown) to return the cantilever 110 to its original, fixed position.

In certain embodiments of the invention, the detector 280 and first 140 and second 195 power supplies are operably coupled to an information processing and control system, such as a computer. In some embodiments, the forces on the cantilever 110 may be precisely balanced by the computer in real time, so that analyte 130 binding is immediately counterbalanced by an increase in voltage to the electromagnet 190. In this case, the cantilever 110 remains in a constant, fixed position. With appropriate calibration, the number of analytes 130 bound to the probe molecules 120 may be determined from the amount of increase in power supplied to the electromagnet 190 required to prevent deflection of the cantilever 110. In some cases, it is possible to detect binding of a single analyte 130 to the cantilever 110 by the disclosed methods.

Example 2

Charge-balanced Cantilever

FIG. 2 illustrates an alternative exemplary apparatus 200 and method for analyte 230 detection and/or identification. The apparatus 200 comprises a cantilever 210 attached to one or more probe molecules 220 that can bind to charged or neutral analytes 230. Binding of charged analytes 230 results in deflection of the cantilever 210 in response to an electrical potential gradient imposed by a first power supply 240 attached to a pair of electrodes 250, 260. Binding of neutral analytes 230 may cause cantilever 210 deflection due to a change in surface tension. Cantilever 210 deflection may be detected by a detection unit comprising a laser 270 and position sensitive photodetector 280.

In the exemplary embodiment of the invention illustrated in FIG. 2, the counterbalancing force is provided by an inducible charge storage layer 290 attached to or incorporated in the cantilever 210. The charge storage layer 290 comprising, for example, a thin layer of semiconductor material or ferroelectric material deposited on the cantilever 210 and covered by an insulating resin, is connected to a second power supply 295. In response to an induced voltage, the charge storage layer 290 accumulates a net charge 296 that can counterbalance the charge associated with the bound analytes 230 or the surface tension associated with binding of analytes 230 in general. By imposing a counterbalancing force, the net force on the cantilever 210 is reduced to zero and the cantilever 210 is maintained in or returned to its original fixed position. As in Example 1, the number of bound analytes 230 may be determined by the amount of power required to maintain the cantilever 210 in a fixed position.

Example 3

Cantilever Balanced by Radiation Pressure

The use of electromagnetic (e.g. light) radiation to apply a force to various objects is known, for example in the construction and use of optical tweezers (e.g. Walker et al., FEBS Lett. 459:39–42, 1999; Bennink et al., Cytometry 36:200–208, 1999; Mehta et al., Science 283:1689–95, 1999; Smith et al., Am. J. Phys. 67:26–35, 1999). FIG. 3 illustrates another exemplary apparatus 300 and method for analyte 330 detection and/or identification.

Alternative geometries are available to provide a radiation pressure counterbalancing force. In embodiments of the invention exemplified in FIG. 3, a transparent object with a curved surface (e.g. a bead 390) and a refractive index that differs from the surrounding medium may be attached to any part of a cantilever 310. A focused light beam 375 can create a force on the transparent object 390 to generate a counterbalancing force. In alternative embodiments of the invention, a light beam 375 may be directed against a planar surface that may be highly reflective. The surface may comprise part or all of a surface of the cantilever 310. Alternatively, the planar surface may be attached to the cantilever 310. The intensity of the light beam 375 may be controlled to adjust the strength of the counterbalancing force. In other alternative embodiments of the invention, two or more light beams 375 may be directed against the same surface of a cantilever 310 or against different surfaces of a cantilever 310 to control the strength of the counterbalancing force. Where a light beam 375 is directed against a planar surface, the light beam 375 may be focused or unfocused. Where a transparent object with a curved surface 390 is used, the light beam may be focused.

The apparatus 300 illustrated in FIG. 3 comprises one or more cantilevers 310 with attached probe molecules 320. The probe molecules 320 can bind to either charged or uncharged target analytes 330. Where the analyte 330 is charged, the cantilever 310 may be flanked by a pair of electrodes 350, 360 attached to a power supply 340 to create an electrical potential gradient. Binding of charged analytes 330 in the presence of an electrical potential gradient will create a force that tends to deflect the cantilever 310. As discussed above, binding of uncharged analytes 330 may deflect the cantilever 310 by inducing changes in surface tension. A laser 365 and photodetector 370 may provide information about the degree of cantilever 310 deflection.

In embodiments of the invention utilizing a curved, transparent object 390 attached to a cantilever 310 (FIG. 3), deflection of the cantilever 310 in response to analyte 320 binding may be counterbalanced by a radiative force, similar to that used with optical tweezers. A laser beam 375 may be focused through an objective lens 380 onto a transparent dielectric sphere or bead 390. The sphere or bead 390 has an index of refraction that is greater than that of the surrounding medium. The objective lens 380 may simultaneously create two or more focal points 385, 395 flanking the sphere or bead 390. Movement of the sphere or bead 390 towards a focal point 385, 395, for example by cantilever 310 deflection, creates a counterbalancing force that tends to restore the cantilever 310 to its fixed position. In alternative embodiments of the invention, the beam path may be changed and/or the objective lens 380 moved to move the focal point(s) 385, 395. In certain embodiments, it is possible to have multiple, continuous focal points 385, 395 along the optical axis.

The counterbalancing force represents a balance between the scattering force and gradient force, as known for optical tweezers. The strength of the counterbalancing force is a function of the intensity of the laser beam 375 and the distance between the bead 390 and the focal point 385, 395. Thus, a computer controlled feedback loop that regulates laser beam 375 intensity, beam path and/or objective lens 380 position in response to cantilever 310 deflection may be used to maintain the cantilever 310 in a fixed position. As discussed above, the strength of the counterbalancing force required to maintain the cantilever 310 in a fixed position is proportional to the number of charged analytes 330 bound to probe molecules 320 attached to the cantilever 310. Although FIG. 3 shows the transparent object 390 attached to one end of the cantilever 310, the skilled artisan will realize that the transparent object 390 may be attached to any part of the cantilever 310.

Example 4

Cantilever Design

Figure 4:
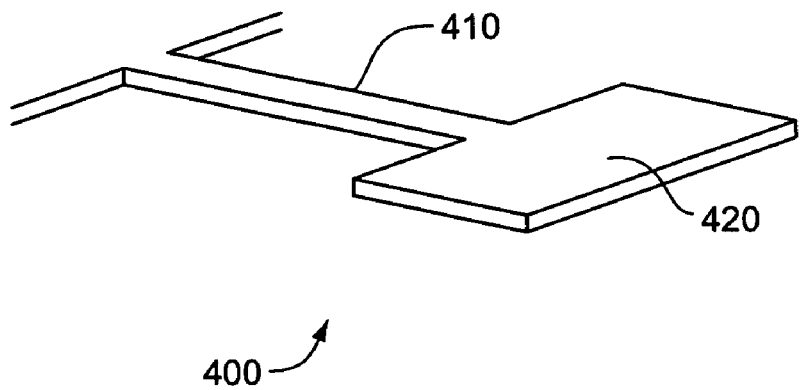
FIG. 4 illustrates an exemplary cantilever 400 (not to scale).
Figure 5:
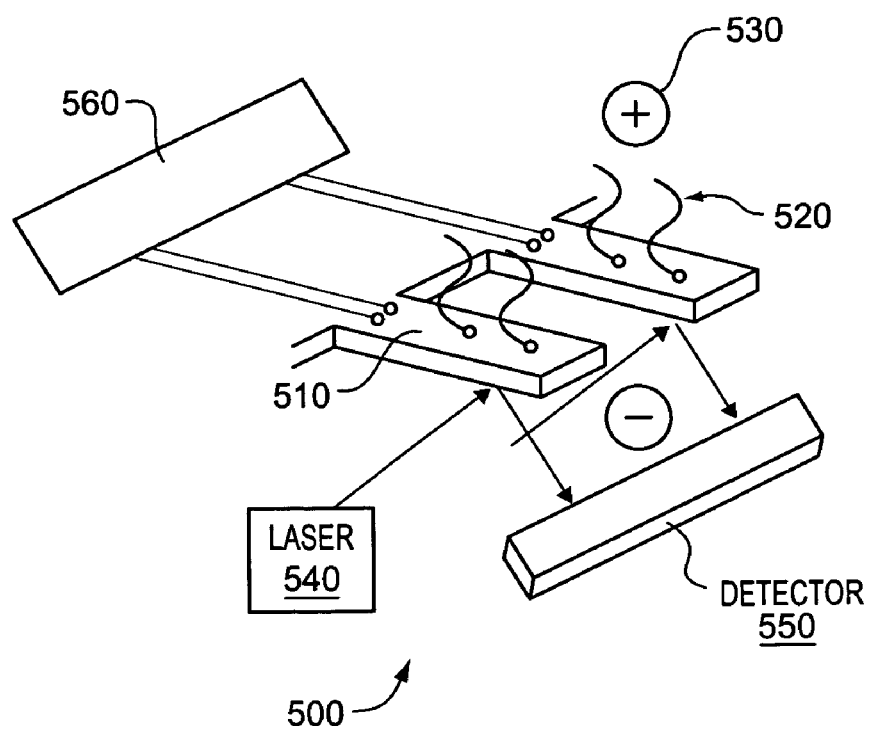
FIG. 5 illustrates an exemplary array 500 of cantilevers 510 (not to scale).

Exemplary cantilever 400, 510 designs are illustrated in FIG. 4 and FIG. 5. FIG. 4 shows a single cantilever 400, comprising a long, thin, narrow bar 410 attached to a wide end 420. Probe molecules 120, 220, 320, 520 would be attached to the end 420 of the cantilever 400. This design would maximize the degree of cantilever 400 deflection in response to analyte 130, 230, 330 binding.

FIG. 5 illustrates an exemplary array 500 of cantilevers 510. Each cantilever 510 contains attached probe molecules 520. In different embodiments of the invention, each cantilever 510 may be attached to identical probe molecules 520 or may be attached to different probe molecules 520. Deflection of the cantilevers 510 may be detected by a laser 540 and position sensitive detector 550. Binding of charged analytes 130, 230, 330 to the probe molecules 520 causes a deflection of the cantilever 510 in response to an imposed electrical potential gradient 530, or in response to a change in surface tension. As discussed in Examples 1 and 2 above, in certain embodiments of the invention a counterbalancing force may be imposed on the cantilevers 510 using a voltage regulator (power supply) 560. Where an array 500 of cantilevers 510 is present, the voltage input to each cantilever 510 may be individually regulated to keep each cantilever 510 balanced in its fixed (neutral) position.

Example 5

One major advantage of direct transduction is it eliminates the requirement that molecules under investigation be previously labeled, for example, with fluorescence or radioactive tags. Another major advantage of restoring the deflected cantilever is to extend the life of the cantilever by reducing stress on the cantilever itself.

In one exemplary method, hybridization experiments are performed in a liquid cell containing a silicon cantilever array immersed in hybridization buffer (J. Fritz et al Translating Biomolecular Recognition into Nanomechanics, Science 14 Apr. 2000, v288, pp. 316–318). The bending of each cantilever is measured in situ, using an optical beam deflection followed by restoration of the cantilever technique. Synthetic 5' thio-modified oligonucleotides with different base sequences are covalently immobilized on a gold-coated side of cantilevers. The functionalization of one cantilever with a 12-mer oligonucleotide and the other with a 16-mer oligonucleotide is performed in parallel under identical conditions. The cantilever arrays are equilibrated in hybridization buffer until the differential signal became stable. Then, the complementary 16-mer oligonucleotide solution is injected into the liquid cell followed by injection of complementary 12-mer oligonucleotide solution. The injections will lead to hybridization of oligonucleotides in solution with the matching oligonucleotides immobilized on the cantilever surfaces. This results in a displacement force required to restore the cantilevers to their original position resulting from an in surface stress between the functionalized gold and the nonfunctionalized Silicon surface, which bends the cantilever. During the entire process, the restoration of the cantilever versus the absolute deflections of individual cantilevers are recorded. Simultaneously, the restoration as a result of the differential signal (deflection of cantilever covered by the 16-mer oligonucletoide minus deflection of the cantilever covered by the 12-mer oligonucleotide.) is extracted and compared.

Non-specific signals from individual cantilevers are removed by extracting the differential signal from two cantilevers. Because all cantilevers of an array are physically identical, the differential signal is sensitive only to the individual cantilevers' ability to recognize complementary oligonucleotides. Non-specific binding bends the cantilevers in parallel thus the restoration force would be identical, leading to no overall differential signal. These experiments will demonstrate that the differential bending is clearly sequence-specific and provides an unambiguous "yes" or "no" response to binding.

For example, a hybridization experiment using two cantilevers functionalized with the sequences 5'-TGCACTA-GACCT-3' (SEQ ID No. 1, 12-mer oligonucleotide), and 5'-TAGCCGATATGCGCAT-3' (SEQ ID No. 2, 16-mer oligonucleotide) is generated. A baseline (interval I) is taken and the complementary 16-mer oligonucleotide 5'-ATCG-GCTATACGCGTA-3' (SEQ ID No. 4, 16-mer oligonucleotide) (1 ml, 400 nM in HB, hybidization buffer) is injected (interval II). The liquid cell is then purged for 20 min with 3 ml of HB. Then, the complementary 12-mer oligonucleotide 5'-ACGTGATCTGGA-3' (SEQ ID No. 3, 12-mer oligonucleotide) (1 ml, 400 nM in HB) is injected (interval III). The liquid cell is again purged 20 min later with 3 ml of HB. The Restoration after Absolute deflection versus time of two individual cantilevers covered with the 16-mer and the 12-mer oligonucleotide will be measured.

Example 6

A crucial test for the analytical ability of nanomechanical transduction is whether a single base mismatch between two DNA sequences can be detected. Thus two cantilevers differing in only one base of their immobilized 12-mer oligonucleotides are made. Injection of the first complementary oligonucleotide will increase the differential of the recovery signal. If the hybridization and its transduction into nanomechanical bending are not sensitive to a single base difference, no differential signal will be recorded. This will be confirmed by injecting the oligonucleotides complementary to the sequence on the second cantilever. The differential signal will be observed between the two 12-mer signal by a difference in the return signal to their starting value. The experiment demonstrates the detection of a single base mismatch by a nanomechanical response, showing that the method has the intrinsic sensitivity required to detect for example SNPs and insertions etc., and suggests capability to determine single base mutations or to sequence DNA by hybridization.

Given that oligonucleotides with a single base mismatch will hybridize to a small extent, the cantilever with the imperfect matching sequence will bend slightly and reduce the amplitude of the differential signal. This difference may be subtracted from the final measured opposing force.

After binding, hybridized oligonucleotides may be chemically denatured by purging the liquid cell with a denaturant such as a high concentration of urea (30% in $H_2O$), which is known to break the hydrogen bonds between complementary bases. This will reestablish the initial conditions of the experiment and enabled the same array to be reused for several additional experiments over several days. By varying the concentration of oligonucleotides in solution, the amplitude of the differential signal will increase with increasing concentration of the oligonucleotide, as expected from the equilibrium character of surface-bound hybridization.

In all experiments, the density of immobilized oligonucleotides is kept constant. It has been shown that a surface coverage of ~$10^{10}$ oligonucleotides per cantilever may be achieved. Optimization of buffer composition and surface immobilization will increase the differential signal of recovery detected. An additional advantage will be using smaller cell volumes and cantilevers that accommodate ~$10^7$ oligonucleotides to greatly decrease the number of molecules needed for an experiment.

Again, this method has important advantages in that it does not require labeling, optical excitation, or external probes and binding is measured in "real-time". Additionally, the transduction process is repeatable when the bound agents are removed (eg. denaturation etc.) allowing the cantilevers to be used more than once. The methodology is compatible with silicon technology (eg. chip technology) and is suited for in situ operation.

Example 7

In this example, detection of bacteria using a resonant-frequency-based mass detection biological sensor will be used. The biological sensor may be composed of an array of low-stress silicon-nitride cantilever beams that are made using bulk micromachining techniques known in the art (Ilic et al, 2000 "Mechanical resonant immunospecific biological detector" Applied Physics Letters 77: 450–452). Signal transduction of the resonant structures is accomplished by measuring the restoration (eg. temperature) signal opposed to the out-of-plane vibrational resonant mode using an optical deflection system. Optical measurements may be by monitoring light reflection from a cantilever (eg. a Dimension 3000 Digital Instruments (DI) atomic-force microscope) and the temperature of a cantilever required to restore it to its original position may be measured by monitoring the resistance change of the heater 610,710. In one example, the reflected laser beam from the cantilever's apex is sensed by a split photodiode, used as a position-sensitive detector (PSD). The A-B signal from the PSD is extracted directly from the DI signal access module using a HP3562A dynamic signal analyzer.

One method for fabricating a cantilever starts with silicon wafers covered with either 320 nm of low-pressure or 600 nm of plasma-enhanced chemical-vapor deposition (LPCVD or PECVD) low-stress silicon nitride. Cantilever thickness may be verified using an ellipsometer (Rudolph Research model 43603). In order to define the resonating beam and cantilever substrate, photolithography is carried out on the frontside and the exposed silicon nitride is etched in a reactive ion etch (RIE) chamber using $CF_4$. Next, backside alignment may be carried out and the back of the cantilever substrate is also defined by RIE. To prevent roughening of the frontside silicon nitride during subsequent KOH etching, 2 μm of PECVD oxide may be deposited. If the backside etching neared the front, PECVD oxide may be removed via a buffered oxide etch solution (eg. 6:1) and the etch continued from both sides until the cantilevers are released. Cantilever lengths will vary from 100 to 500 μm.

The use of a high-pressure $CO_2$ critical-point dryer allows the removal of longer (>300 μm) cantilevers by reducing the surface tension of that solution, which tends to cause breaking of the cantilevers. The shorter (<300 μm) cantilevers may be used for experiments such as cell detection.

After releasing, cantilevers are immersed into a solution containing a substrate for example an antibody such as *E. coli* serotype O157:H7 antibodies (Kirkegaard & Perry Laboratories Inc., Gaithersburg, Md.) for 5 min. The cantilevers are then rinsed in deionized water and dried by nitrogen. The average antibody thickness may be obtained by Tapping-mode atomic-force topographs, in conjunction with a surface scratching scanning probe microscope technique using a diamond-coated tapping-mode-etched silicon probe, (for example the data revealed may be 40 nm across ten substrates). Cantilevers may then be immersed into a buffer solution containing different concentrations of the antigen, for example *E. coli* cells ranging from $10^6$ to $10^9$ *E. coli* cells/ml. The cells are incubated at room temperature for 15 min. Devices are first rinsed in a solution (eg. 0.05% Tween) to remove any loosely bound cells, then in deionized water and then nitrogen dried. Cell binding may be monitored (eg. Leo 982 scanning electron microscope (SEM)) to evaluate the topography of the resonator after cell binding.

In order to determine the mass bound to each of the cantilevers in the array, frequency spectra will be taken before and after an introduction of a new component to a cantilever for example binding of the cells to the antibodies.

When a binding event occurs, the additional cell mass loading will shift the resonant frequency of the micromechanical oscillator. To confirm the specificity of the binding events, cantilevers without the presence of the new component such as the immobilized antibodies may be treated with a buffer solution containing cells. These cells will not bind to the cantilevers, and in turn, the resonant frequency of the oscillators remains unchanged. Additional experiments may be used to test the specificity of the new component for example applying *Salmonella typhimurium* cells to the *E. coli* antibody coated cantilevers. Any binding event will be confirmed optically and thermally. In this example, the specificity of the application may be analyzed against any other cellular organism.

All of the METHODS and APPARATUS 100, 200, 300 disclosed and claimed herein can be made and executed without undue experimentation in light of the present disclosure. It will be apparent to those of skill in the art that variations may be applied to the METHODS and APPARATUS 100, 200, 300 described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. A method of detecting and/or identifying analytes comprising:
   a) obtaining one or more probe molecules that bind to one or more target analytes;
   b) attaching the probe molecules to one or more cantilevers having an original position;
   c) exposing the probe molecules to at least one sample suspected of containing one or more target analytes;
   d) deflecting the cantilever;
   e) imposing a counterbalancing force to restore the cantilever to its original position; and
   f) detecting and/or identifying the analytes from the magnitude of the counterbalancing force required to maintain the cantilever in its original position.

2. The method of claim 1, wherein the target analytes have a net electrical charge.

3. The method of claim 2, wherein the cantilever is deflected in response to an electrical potential gradient.

4. The method of claim 1, wherein the cantilever is deflected in response to a change in surface tension.

5. The method of claim 1, wherein the target analytes are selected from the group consisting of an amino acid, peptide, polypeptide, protein, glycoprotein, lipoprotein, antibody, nucleoside, nucleotide, oligonucleotide, nucleic acid, sugar, carbohydrate, oligosaccharide, polysaccharide, fatty acid, lipid, hormone, metabolite, growth factor, cytokine, chemokine, receptor, neurotransmitter, antigen, allergen, antibody, substrate, metabolite, cofactor, inhibitor, drug, pharmaceutical, nutrient, biohazardous agent, infectious agent, prion, vitamin, heterocyclic aromatic compound, carcinogen, mutagen, waste product, virus, bacterium, *Salmonella, Streptococcus, Legionella, E. coli, Giardia, Cryptosporidium, Rickettsia*, spore, mold, yeast, algae, amoebae, dinoflagellate, unicellular organism, pathogen, prion and a cell.

6. The method of claim 1, wherein the probe molecules are selected from the group consisting of antibodies, antibody fragments, single-chain antibodies, genetically engineered antibodies, oligonucleotides, polynucleotides, nucleic acids, nucleic acid analogues, peptide nucleic acids, proteins, peptides, synthetic peptides, binding proteins, receptor proteins, transport proteins, lectins, substrates, inhibitors, activators, ligands, hormones, neurotransmitters, growth factors and cytokines.

7. The method of claim 1, wherein the probe molecules are oligonucleotides and the target analytes are nucleic acids.

8. The method of claim 1, wherein the target analytes are proteins or peptides.

9. The method of claim 8, wherein the probe molecules are antibodies, antibody fragments, genetically engineered antibodies or single chain antibodies.

10. The method of claim 1, wherein the counterbalancing force is magnetic.

11. A method of detecting and/or identifying analytes comprising:
    a) obtaining one or more probe molecules that bind to one or more target analytes;
    b) attaching one or more target analytes to one or more cantilevers having an original position;
    c) exposing the target analytes to the probe molecules;
    d) deflecting the cantilever;
    e) imposing a counterbalancing force to restore the cantilever to its original position; and
    f) detecting and/or identifying the analytes from the magnitude of the counterbalancing force required to maintain the cantilever in its original position.

12. The method of claim 11, wherein the target analytes are selected from the group consisting of an amino acid, peptide, polypeptide, protein, glycoprotein, lipoprotein, antibody, nucleoside, nucleotide, oligonucleotide, nucleic acid, sugar, carbohydrate, oligosaccharide, polysaccharide, fatty acid, lipid, hormone, metabolite, growth factor, cytokine, chemokine, receptor, neurotransmitter, antigen, allergen, antibody, substrate, metabolite, cofactor, inhibitor, drug, pharmaceutical, nutrient, biohazardous agent, infectious agent, prion, vitamin, heterocyclic aromatic compound, carcinogen, mutagen, waste product, virus, bacterium, *Salmonella, Streptococcus, Legionella, E. coli, Giardia, Cryptosporidium, Rickettsia*, spore, mold, yeast, algae, amoebae, dinoflagellate, unicellular organism, pathogen and a cell.

13. The method of claim 11, wherein the probe molecules are selected from the group consisting of antibodies, antibody fragments, single-chain antibodies, genetically engineered antibodies, oligonucleotides, polynucleotides, nucleic acids, nucleic acid analogues, peptide nucleic acids, proteins, peptides, binding proteins, receptor proteins, transport proteins, lectins,substrates, inhibitors, activators, ligands, hormones, neurotransmitters, growth factors and cytokines.

* * * * *

SEQUENCE LISTING

```
<160> NUMBER OF SEQ ID NOS: 4

<210> SEQ ID NO 1
<211> LENGTH: 12
<212> TYPE: DNA
<213> ORGANISM: Artificial
<220> FEATURE:
<223> OTHER INFORMATION: Oligonucleotide

<400> SEQUENCE: 1
tgcactagac ct                                                          12

<210> SEQ ID NO 2
<211> LENGTH: 16
<212> TYPE: DNA
<213> ORGANISM: Artificial
<220> FEATURE:
<223> OTHER INFORMATION: oligonucleotide

<400> SEQUENCE: 2
tagccgatat gcgcat                                                      16

<210> SEQ ID NO 3
<211> LENGTH: 12
<212> TYPE: DNA
<213> ORGANISM: Artificial
<220> FEATURE:
<223> OTHER INFORMATION: Oligonucleotide

<400> SEQUENCE: 3
acgtgatctg ga                                                          12

<210> SEQ ID NO 4
<211> LENGTH: 16
```

```
-continued

<212> TYPE: DNA
<213> ORGANISM: Artificial
<220> FEATURE:
<223> OTHER INFORMATION: Oligonucleotide

<400> SEQUENCE: 4
atcggctata cgcgta                                                      16
```